United States Patent [19]

Clitherow et al.

[11] Patent Number: 4,536,508

[45] Date of Patent: Aug. 20, 1985

[54] TRIAZOLEAMINE DERIVATIVES HAVING HISTAMINE H$_2$-ANTAGONIST PROPERTIES

[75] Inventors: John W. Clitherow, Sawbridgeworth; Barry J. Price, Hertford; John Bradshaw; Michael Martin-Smith, both of Ware; John W. M. Mackinnon, Royston; Duncan B. Judd, Ware; Roger Hayes, Welwyn, all of England

[73] Assignee: Glaxo Group Limited, London, England

[21] Appl. No.: 467,896

[22] Filed: Feb. 18, 1983

Related U.S. Application Data

[63] Continuation of Ser. No. 125,848, Feb. 29, 1980, abandoned.

[30] Foreign Application Priority Data

Mar. 2, 1979 [GB] United Kingdom ............... 7907423

[51] Int. Cl.$^3$ ............... A61K 31/41; C07D 249/14; C07D 401/10; C07D 413/10
[52] U.S. Cl. ............... 514/383; 260/245.5; 514/212; 514/230; 514/232; 514/234; 514/237; 514/326; 514/340; 514/384; 544/132; 546/210; 546/276; 548/263; 548/265; 548/266

[58] Field of Search ............... 548/263, 265, 266; 546/210, 276; 544/132; 260/245.5; 424/263, 267, 269, 248.51, 248.52, 248.55, 248.56, 248.57

[56] References Cited

U.S. PATENT DOCUMENTS 4,128,658 12/1978 Price et al. ............... 424/285
4,323,566 4/1982 Clitherow et al. ............... 548/267

FOREIGN PATENT DOCUMENTS 867105 11/1978 Belgium ............... 424/267
867106 11/1978 Belgium ............... 424/267
1419994 1/1976 United Kingdom ............... 548/269
2003471 3/1979 United Kingdom ............... 424/269

*Primary Examiner*—Alton D. Rollins
*Attorney, Agent, or Firm*—Bacon & Thomas

[57] ABSTRACT

The invention relates to compounds of the general formula (I)

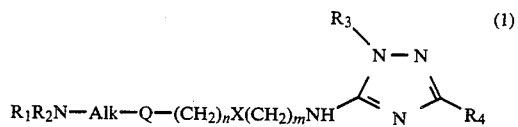

and physiologically acceptable salts, hydrates and bioprecursors thereof, which show pharmacological activity as selective histamine H$_2$-antagonists.

25 Claims, No Drawings

TRIAZOLEAMINE DERIVATIVES HAVING HISTAMINE H₂-ANTAGONIST PROPERTIES

This application is a continuation of application Ser. No. 125,848, filed Feb. 29, 1980, now abandoned.

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit.J.Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of the histamine on the contraction frequency of isolated guinea pig right atrium but do not modify histamine induced contractions of isolated gastrointestinal smooth muscle which are mediated via $H_1$-receptors. Certain compounds according to the invention have the advantage of an extended duration of action.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator, Thus they may be used for example, either alone or in combination with other active ingredients in the treatment of allergic and inflammatory conditions of the skin.

The present invention provides compounds of the general formula (I)

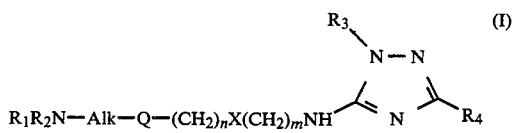

and physiologically acceptable salts, hydrates and bioprecursors thereof,
in which
$R_1$ and $R_2$ which may the same or different, each represent hydrogen, $C_{1-10}$ alkyl, cycloalkyl, alkenyl, alkynyl, aralkyl, trifluoroalkyl, or alkyl substituted by hydroxy, alkoxy, amino, alkylamino, dialkylamino or cycloalkyl or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl groups, e.g. methyl or a hydroxy group and/or may contain another heteroatom, e.g. oxygen or sulphur;
Alk represents a straight or branched alkylene chain of 1 to 6 carbon atoms, preferably 1 to 4 carbon atoms;
Q represents a furan or thiophen ring in which incorporation into the rest of the molecule is through bonds at the 2- and 5-positions, the furan ring optionally bearing a further substituent $R_6$ adjacent to the group $R_1R_2N$—Alk—, or Q represents a benzene ring
in which
incorporation into the rest of the molecule is through bonds at the 1- and 3- or 1- and 4-positions;
$R_6$ represents halogen or $C_{1-4}$ alkyl which may be substituted by hydroxy or $C_{1-4}$ alkoxy;
X represents —CH₂—, —O—, —S— or

where
$R_5$ represents hydrogen or methyl;
n represents zero, 1 or 2;
m represents 2, 3 or 4;
$R_3$ represents hydrogen, alkyl, alkenyl, aralkyl, hydroxyalkyl with at least two carbon atoms, alkoxyalkyl or aryl; and
$R_4$ represents hydrogen, alkyl, alkenyl, aryl, aralkyl, hydroxyalkyl, acyloxyalkyl, alkoxyalkyl, aryloxyalkyl, aralkyloxyalkyl, aminoalkyl, alkylaminoalkyl, dialkylaminoalkyl, hydroxy, alkoxy, alkylthio or halogen.

When X represents an oxygen atom or

and
n is zero, then Q preferably represents benzene.

The term "alkyl" as a group or part of a group means that the group is straight or branched and, unless otherwise stated, has preferably 1 to 6 carbon atoms, and in particular 1 to 4 carbon atoms, e.g. methyl or ethyl, and the terms "alkenyl" and "alkynyl" mean that the group has preferably 3 to 6 carbon atoms. The term "cycloalkyl" means that the group has 3 to 8 carbon atoms.

The term "aryl" as a group or part of a group preferably means phenyl or substituted phenyl, for example phenyl substituted with one or more $C_{1-3}$ alkyl or alkoxy groups or halogen atoms e.g. fluorine. The acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl.

According to one aspect the invention provides compounds according to formula (I) and physiologically acceptable salts, hydrates and bioprecursors thereof, in which
$R_1$ and $R_2$ are as defined in formula (I) except alkynyl or alkyl substituted by cycloalkyl;
$R_4$ represents hydrogen, alkyl, alkenyl, aryl, aralkyl, hydroxyalkyl, alkoxyalkyl, aryloxyalkyl, aminoalkyl, alkylaminoalkyl, dialkylaminoalkyl, hydroxy, alkoxy or halogen; provided that when X represents an oxygen atom or —NR₅— and when n is zero then Q represents benzene.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, fumarates, tartrates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers.

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg. to 1 g per day, preferably 5 to 250 mg per day, dependant upon the condition of the patient being treated.

In the compounds according to the invention, preferably the total of m+n is 3 or 4.

Preferably Q is benzene incorporated into the rest of the molecule through bonds at the 1- and 3-positions. In the case where Q is benzene, preferably n is zero, X is oxygen and m is 3 or 4. If Q is furan, substituted furan or thiophen, preferably n is 1, X is sulphur and m is 2.

Preferably $R_1$ represents hydrogen or $C_{1-4}$ alkyl and $R_2$ represents $C_{3-5}$ alkenyl, $C_{5-7}$ cycloalkyl, benzyl, $C_{1-8}$ alkyl or $C_{1-4}$ alkyl substituted by $C_{1-3}$ alkoxy, hydroxy, di-$C_{1-3}$ alkylamino or trifluoromethyl or $R_1$ and $R_2$ together with the nitrogen atom to which they are attached form a ring with 5 to 8 members and optionally containing one double bond and/or substituted by hydroxy or one or two $C_{1-3}$ alkyl group(s). More preferably $R_1$ and $R_2$ are $C_{1-3}$ alkyl, e.g. methyl or $R_1$ and $R_2$ together with the nitrogen atom to which they are attached form a heterocyclic ring which is pyrrolidine, piperidine optionally substituted in the 4-position by $C_{1-3}$ alkyl e.g. methyl or hydroxy, tetrahydropyridine, morpholine, 2,6-dialkylmorpholine, hexamethyleneimine or heptamethylenimine. Most preferably the heterocyclic ring is piperidine.

Preferably $R_3$ represents hydrogen, alkyl or $C_{2-4}$ hydroxyalkyl. More preferably $R_3$ represents methyl.

Preferably $R_4$ represents hydrogen, alkyl, hydroxyalkyl, alkoxyalkyl, acyloxyalkyl, aralkyl, aralkyl or hydroxy. More preferably $R_4$ is hydroxyalkyl, e.g. hydroxymethyl, benzyl, hydroxy, alkoxyalkyl, e.g. methoxy methyl. Most preferably $R_4$ is hydroxymethyl.

Preferably Alk is $CH_2$.

A particularly preferred group of compounds of formula (I) are those of formula (II)

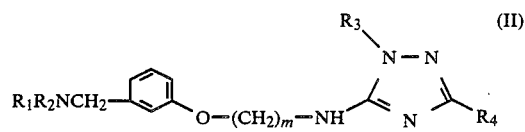

where $R_1$ and $R_2$ are methyl groups or together with the nitrogen atom to which they are attached form a pyrrolidino, piperidino or hexamethyleneimino group; m is 3 or 4, $R_3$ is hydrogen or methyl; and $R_4$ is a hydroxyalkyl, alkoxyalkyl, benzyl or hydroxy.

Particularly preferred compounds are
(1) 1-methyl-5-[[4-[3-(1-piperidinylmethyl)phenoxy]-butyl]amino]-1H-1,2,4-triazole-3-methanol
(2) 1-methyl-5-[[3-[3-(1-piperidinylmethyl)phenoxy]-propyl]amino]-1H-1,2,4-triazole-3-methanol
(3) 3-methoxymethyl-1-methyl-5-[[4-[3-(1-piperidinyl methyl)phenoxy]butyl]amino]-1H-1,2,4-triazole.
(4) 3-phenylmethyl-N-[3-[3-(dimethylaminomethyl)-phenoxy]propyl]-1H-1,2,4-triazole-5-amine
(5) 5-[4-[3-(1-piperidinylmethyl)phenoxy]butyl]amino-1H-1,2,4-triazole-3-methanol
(6) 3-phenylmethyl-N-[3-[3-(1-piperidinylmethyl)-phenoxy]propyl]-1H-1,2,4-triazole-5-amine
(7) 5-[[3-[3-(1-piperidinylmethyl)phenoxy]propyl-]amino]-1H-1,2,4-triazole-3-one
and their physiologically acceptable salts.

Of the above mentioned compounds, compounds Nos. (1) (2) and (3) and their salts are particularly preferred.

It will be appreciated that in the methods for the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and-/or $R_2$ in intermediates used to prepare compounds of formula (1) are hydrogen atoms and/or when $R_3$ in intermediates is an alkyl group bearing a hydroxy substituent and/or when $R_4$ in certain intermediates is an alkyl group bearing a hydroxyl or a primary or secondary amino substituent. Standard protection and deprotection procedures can be employed, for example formation of phthalimide (in the case of primary amines), benzyl, benzyloxycarbonyl or trichloroethoxycarbonyl derivatives. Subsequent cleavage of the protecting group is achieved by conventional procedures. Thus a phthalimide group may be cleaved by treatment with a hydrazine e.g. hydrazine hydrate or a primary amine, for example methylamine; benzyl or benzyloxycarbonyl derivatives may be cleaved by hydrogenolysis in the presence of a catalyst, e.g. palladium, and trichloroethoxycarbonyl derivatives may be cleaved by treatment with zinc dust.

In describing the processes which may be used for preparing the compounds of formula (1) or intermediates useful in the preparation thereof, any of $R_1$ to $R_{11}$, Alk,Q,X,Y,n and m in the various formulae are as defined in formula (1) unless otherwise stated.

Compounds according to formula (I) in which $R_4$ represents a halogen atom or a hydrogen atom may be prepared from the corresponding diazonium salt (III)

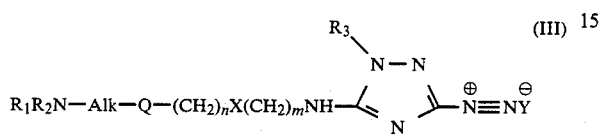

in which $R_1$, $R_2$ and $R_3$ are as defined in formula (I) or are groups convertible thereto and $Y^{\ominus}$ is the anion corresponding to the acid in the diazotisation reaction. Thus treatment of the diazonium salt (III) with a concentrated mineral acid such as sulphuric acid or hypophosphorous acid in a solvent such as ethanol gives the compound of formula (I) in which $R_4$ represents hydrogen. Similarly the reaction of the diazonium salt (III) with hydrochloric acid in the presence of chloride e.g. aqueous cuprous chloride, at elevated temperature gives the compound of formula (I) in which $R_4$ represents a chlorine atom.

Compounds of formula (I) in which $R_4$ is other than a halogen atom or an alkoxy, alkylthio or acyloxyalkyl group may be prepared by cyclisation of a compound of formula (IV)

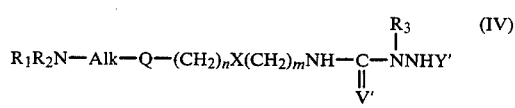

in which V' is

and Y' is hydrogen where V is oxygen or sulphur and $R_4'$ is a group as defined for $R_4$ or a group convertible thereto under the conditions of the cyclisation reaction or represents halogen or alkoxy; or V' is NH and Y' is

where Y is sulphur, oxygen or NH except that when $R_4'$ is halogen or alkoxy Y cannot be NH; or V' is sulphur or oxygen and Y' is

It should be noted that when V' is sulphur in compound (IV) this compound is tautomeric with the thiol (V).

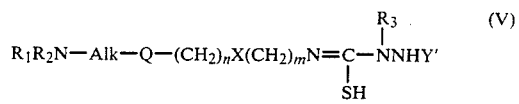

and the corresponding S-alkyl, e.g. S-methyl, derivatives may also be used in the cyclisation.

Thus for example compounds according to formula (I) in which $R_4$ is other than a halogen atom or an alkoxy, alkythio, or acyloxyalkyl group may be prepared by thermal cyclisation of a compound of formula (V1)

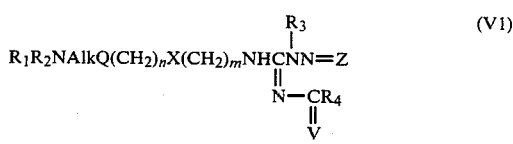

where V represents sulphur or more preferably oxygen and Z represents two hydrogen atoms in the absence or presence or a solvent, e.g. acetone or water.

It may be convenient to prepare compounds of formula (V1) in which Z represents two hydrogen atoms in situ by treating a compound of formula (V11) where Z represents a divalent protecting group which can readily be removed to yield two hydrogen atoms, for example a benzylidene group, with an acid, e.g. hydrochloric acid, preferably with heating and under such conditions cyclisation to give compounds of formula (I) will normally occur.

In a method for preparing the intermediate (V1) a compound of formula (V11)

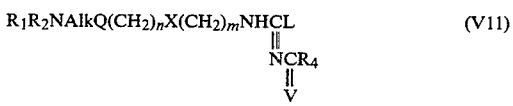

where V is oxygen or sulphur and L is a leaving group such as alkylthio may be reacted with hydrazine $R_3NHN{=}Z$ where Z is as defined above, followed by removal of the protecting group where necessary. Compounds of formula (V11) may be prepared by treating a diamine of formula (VIII)

with a compound of formula (IX)

where L and V are as defined above.

As a further possibility the diamine of formula (VIII) may be reacted with a compound of formula (X)

where L, V and Z are as defined above, in the absence or presence of a solvent such as acetone or acetonitrile at a temperature of from room temperature to 70° C. Subsequent removal of the protecting group where appropriate then gives the intermediate (V1).

Compounds of formula (X) may be prepared by acylating a compound of formula (X1)

  (X1)

with for example an acid chloride R$_4$COCl. The compound of formula (X1) may be prepared by treating a compound

with the appropriate hydrazine R$_3$NHN=Z

When preparing compounds of formula (I) in which R$_4$ is a hydroxyalkyl group it is preferable that in the intermediates (V1), (V11) and (X) the hydroxy group is in protected form, e.g. as an acyloxy derivative such as an alkanoyloxy or aroyloxy derivative. The protecting group will normally be removed during the cyclisation process.

In a further embodiment of the cyclisation of compounds of formula (IV) compounds of formula (I) in which R$_4$ is other than a halogen atom, or an alkoxy, alkylthio or acyloxyalkyl may also be prepared by cyclisation of a compound of formula (X11)

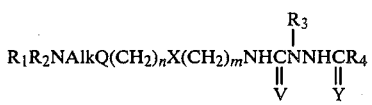  (X11)

where V is NH and Y is sulphur, oxygen or NH, or V is sulphur or oxygen and Y is NH. The reaction is preferably carried out by heating the compound (X11) in a suitable solvent such as acetonitrile or dimethylformamide.

In general intermediates of formula (X11) may be prepared by methods analogous to those described in British Patent Specification No. 2023133. A.

In a particularly convenient embodiment of the above process an intermediate of formula (X11) in which V is NH and Y is oxygen may be prepared in situ by the reaction of an aminoguanidine (X1 II)

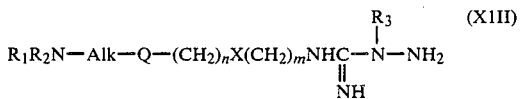  (XIII)

with an acid R$_4$COOH or with an activated derivative thereof as defined above.

The acid and the amino guanidine (X1 II) may be heated together, under which conditions cyclisation of the intermediate (X11) takes place directly to give a compound of formula (I). In the case of an activated derivative an aprotic solvent, e.g. tetrahydrofuran may be used at temperatures from ambient to reflux. When using an acyl chloride as the activated derivative the reaction may also be carried out in the presence of a base e.g. potassium hydroxide.

Compounds of formula (I) may be prepared by reducing a compound of formula (XIV)

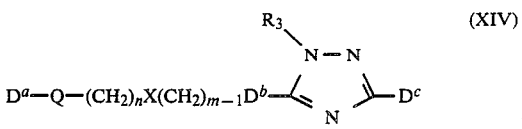  (XIV)

in which at least one of D$^a$, D$^b$ and D$^c$ represents a reducible group and the other(s) take the appropriate meaning corresponding to formula (I).

Thus D$^9$ may represent R$_1$R$_2$NAlk or a group convertible thereto under reducing conditions;
D$^b$ represents —CH$_2$NH—, CONH— or —CH=N—; and
D$^c$ represents R$_4$ or a group convertible thereto under reducing conditions.

Examples of the type of group that may be reduced are an amide, imide, imine, ester, aldehyde, ketone or nitrile group. Examples of the type of group D$^a$ which may be converted into the group R$_1$R$_2$NAlk under reducing conditions are: an amide grouping R$_1$R$_2$NCO(CH$_2$)$_p$ where p is 0,1,2,3,4 or 5 or R$_1{}^a$CONR$_2$Alk—where R$_1{}^a$CO represents a group which is reducible into R$_1$; an aralkylidenaminoalkyl grouping; a nitrile group NC(CH$_2$)$_p$ where p is 0,1,2,3,4 or 5; or an aldehyde group. When D$^a$ is an aldehyde group the conversion into R$_1$R$_2$NAlk under reducing conditions is carried out in the presence of an appropriate amine R$_1$R$_2$NH, the reaction proceeding by reductive alkylation.

Examples of the group D$^c$ which may be converted into R$_4$ under reducing conditions are: an amide grouping —(CH$_2$)$_{q-1}$CONR$_a$R$_c$ where R$_a$ represents hydrogen, alkyl, or aralkyl, R$_c$ represents hydrogen or alkyl and q is an integer from 1 to 6 inclusive with the possibility that the alkylene chain (CH$_2$)$_{q-1}$ may be straight or branched, or an amide grouping —(CH$_2$)$_q$NR$_a$COR$_b{}'$ where R$_a$ is as defined above, R$_b$ is alkyl and COR$_b{}'$ is a group which is reducible into R$_b$ and q is as defined above with the possibility that the alkylene chain (CH$_2$)$_q$ may be straight or branched; a nitrile group —(CH$_2$)$_{q-1}$CN; an aldehyde group —(CH$_2$)$_{q-1}$CHO; an ester group —(CH$_2$)$_{q-1}$CO$_2$R$_7$ where q is as defined above and R$_7$ is an alkyl group, or a ketone group —(CH$_2$)$_r$COR$_7$ where r is 0 to 4 and R$_7$ is an alkyl group and the total number of carbon atoms in (CH$_2$)$_r$ and R$_7$ is not more than 5.

D$^a$ and /or D$^c$ may also represent an aminoalkyl group, in which case the compound of formula (XIV) is reacted with an appropriate aldehyde or ketone under reducing conditions to give the group R$_1$R$_2$NAlk— and/or R$_4$, the reaction proceeding by reductive alkylation.

A variety of reducing agents may be used in the above process.

Thus amides, imides, imines, esters, aldehydes, ketones and nitriles may conveniently be reduced using for example lithium aluminium hydride or aluminium hydride in a solvent such as tetrahydrofuran, dioxan or diethyl ether. Imines, aldehydes and ketones may be reduced using an alkali or alkaline earth metal borohydride e.g. sodium borohydride or by treatment with hydrogen and a suitable metal catalyst such as platinum, palladium or Raney nickel, in a suitable solvent such as a alkanol e.g. methanol or ethanol. Imines may also be reduced using formic acid.

In the particular process involving reductive alkylation of an amine with an aldehyde or ketone the reaction is conveniently carried out without isolation of the intermediate which is subsequently reduced using for example sodium borohydride, or hydrogen in the presence of a suitable catalyst.

Thus in one embodiment of the reduction process compounds of formula (I) in which $R_4$ is other than an acyloxyalkyl group may be prepared by reduction of an amide of formula (XIV) in which (a) $D^a$ represents $R_1R_2NCO(CH_2)_p$ or $R_1{}^aCONR_2Alk$, $D^b$ represents —$CH_2NH$— and $D^c$ represents $R_4$; or (b) $D^a$ represents $R_1R_2NAlk$, $D^b$ represents —$CONH$— and $D^c$ represents $R_4$; or (c) $D^a$ represents $R_1R_2NAlk$, $D^b$ represents —$CH_2NH$— and $D^c$ represents $(CH_2)_{q\text{-}1}CONR_aR_c$ or $(CH_2)_qNHCOR_{b'}$; where p,q, $R_a,R_c,R_1{}^a$ and $R_{b'}$ are as defined above, with a suitable reducing agent such as lithium aluminium hydride or an aluminium hydride in a solvent such as tetrahydrofuran, dioxan or diethyl ether.

A particularly useful amide of formula (XIV) is that in which $D^a$ represents $R_1R_2NAlk$, $D^b$ represents —$CONH$— and $D^c$ represents $R_4$.

In a further embodiment of the reduction process a compound of formula (XIV) in which $D^a$ or $D^c$ is a cyanoalkyl group $NC(CH_2)_p$ or $(CH_2)_{q\text{-}1}CN$ respectively may be reduced to a compound of formula (I) in which $R_1R_2NAlk$ is a primary aminoalkyl group or $R_4$ is a primary aminoalkyl group $(CH_2)_{q\text{-}1}CH_2NH_2$. Reduction may be effected using for example lithium aluminium hydride in a solvent such as diethyl ether or tetrahydrofuran.

In a further embodiment of the reduction process compounds of formula (I) may be prepared by reduction of an amine of formula (XIV) in which (a) $D^a$ represents an aralkylidenaminoalkyl group, $D^b$ represents —$CH_2NH$— and $D^c$ represents $R_4$; or (b) $D^a$ represents $R_1R_2NAlk$, $D^b$ represents —$CH=N$— and $D^c$ represents $R_4$; with a suitable reducing agent such as a metal hydride, e.g. an alkali or alkaline earth metal borohydride, such as sodium borohydride, in a solvent such as an alkanol, e.g. methanol or ethanol, or aluminium hydride or lithium aluminium hydride in a solvent such as tetrahydrofuran or dioxan. The imine (XIV) may also be reduced with hydrogen and a suitable metal catalyst such as platinum, in a solvent such as an alkanol e.g. methanol or ethanol.

A particularly useful imine of formula (XIV) is that in which $D^a$ is $R_1R_2NAlk$, $D^b$ is —$CH=N$— and $D^c$ is $R_4$.

The process involving reductive alkylation of an amine with an aldehyde or ketone to give the compounds of formula (I), without isolation of any intermediate, is also part of this embodiment. Thus, for example compounds of formula (I) in which Alk represents $CH_2$ may be prepared from the compound (XIV) in which $D^a$ represents CHO, $D^b$ represents —$CH_2NH$— and $D^c$ represents $R_4$, by reaction with ammonia or an amine $R_1R_2NH$ in a solvent, e.g. tetrahydrofuran or an alkanol such as ethanol or methanol, followed by reduction e.g. with a hydride reducing agent such as an alkali or alkaline earth metal borohydride, e.g. sodium borohydride, or aluminium hydride or lithium aluminium hydride or with hydrogen and a metal catalyst e.g. palladium or platinum.

In another embodiment of the reduction process, a compound of formula (I) in which $R_4$ represents a hydroxyalkyl group may be prepared from a compound of formula (XIV) in which $D^c$ is a group that may be reduced to a hydroxyalkyl group, e.g. an ester, aldehyde, or ketone, $D^a$ is $R_1R_2NAlk$ and $D^b$ is —$CH_2NH$—. Thus a compound of formula (XIV) in which $D^c$ has the meaning $(CH_2)_{q\text{-}1}CO_2R_7$ may be reduced using for example lithium aluminium hydride to give a compound of formula (I) in which $R_4$ is the group —$(CH_2)_{q\text{-}1}CH_2OH$. Compounds of formula (XIV) in which $D^c$ has the meaning $(CH_2)_{q\text{-}1}CHO$ or $(CH_2)_rCOR_7$ may be reduced using for instance sodium borohydride or lithium aluminium hydride to give a compound of formula (I) in which $R_4$ is the group $(CH_2)_{q\text{-}1}CH_2OH$ or $(CH_2)_rCHOHR_7$ where q,r and $R_7$ are as defined above.

In certain instances it is convenient to reduce for example more than one of the groups $D^a$, $D^b$ and $D^c$ simultaneously. Thus for example compounds of formula (XIV) in which $D^c$ represents $(CH_2)_{q\text{-}1}CO_2R_7$ or $(CH_2)_{q\text{-}1}CONR_aR_c$ and $D^b$ is the group —$CONH$— and $D^a$ is $R_1R_2NAlk$ may be reduced using for example lithium aluminium hydride to give compounds of formula (I) in which $R_4$ is the group $(CH_2)_qOH$ or $(CH_2)_qNR_aR_c$ respectively, where q, $R_a$ and $R_c$ are defined above.

Amides and imines of formula (XIV) where $D^b$ is —$CONH$— or —$CH=N$—, $D^a$ is $R_1R_2NAlk$ and $D^c$ is $R_4$ or a group convertible thereto may be prepared by the reaction of an activated derivative of a carboxylic acid or of an aldehyde (XV)

$$R_1R_2N\text{—}Alk\text{—}Q\text{—}(CH_2)_nX(CH_2)_{m\text{-}1}G \qquad (XV)$$

where G is $CO_2H$ or CHO respectively with the appropriate amino triazole (XVI)

(XVI)

where U is $NH_2$ and $R_4$ is as defined in formula (I) or is a group convertible thereto, using methods analogous to those described in British Patent Specification No. 2023133 A.

Aldehydes and carboxylic acids of formula (XV) may be prepared from an appropriate starting material (XVII)

$$R_1R_2NAlkQ(CH_2)_nXH \qquad (XVII)$$

in which X is other than $CH_2$.

Thus for example a compound $R_1R_2NAlkQOH$ may be treated with a haloalkyl nitrile $Hal(CH_2)_{m\text{-}1}CN$ in a solvent such as dimethylformamide and in the presence of a base e.g. sodium hydride, to give the corresponding compound $R_1R_2NAlkQO(CH_2)_{m\text{-}1}CN$. Subsequent reduction using for example hydrogen in the presence of Raney nickel affords the corresponding aldehyde which may conveniently be isolated as its semicarbazone. The desired aldehyde (XV) may then be generated by treatment with hydrochloric acid and aqueous formaldehyde.

Alternatively treatment of the compound $R_1R_2$—$NAlkQOH$ with an alkyl haloester $Hal(CH_2)_{m\text{-}1}CO_2Alk$ affords the ester $R_1R_2NAlkQO(CH_2)_{m\text{-}}$ 1CO₂Alk, which may then be hydrolysed (e.g. by using potassium hydroxide in aqueous ethanol) to give the corresponding carboxylic acid (XV).

The triazole (XVI) may be prepared by standard methods such as those described by F. Kurzer and L. E. A. Godfrey, Angew.Chem.International Edition 2, 459–476 (1963) and K. T. Potts, Chem.Reviews 61,87 (1961).

The compunds of formula (XIV) in which $D^a$ represents $R_1R_2NCO(CH_2)_p$ or CHO, $D_b$ represents —CH₂NH and $D^c$ represents $R_4$ may be prepared from an amine of formula (XVIII)

W—Q—(CH₂)ₙX—(CH₂)ₘ—NH₂      (XVIII)

in which W represents the group $R_1R_2NCO(CH_2)_p$ or a protected aldehyde group e.g. a cyclic ketal such as an ethylene ketal, by methods analogous to those already described for preparing the corresponding compounds of formula (I).

The compounds of formula (XIV) in which $D^a$ has the meaning $R_1{}^aCONR_2Alk$— and/or $D^c$ has the meaning $(CH_2)_qNR_aCOR_b{}'$ may be prepared by treating the corresponding compounds in which $D^a$ is HNR₂Alk— and/or $D^c$ is $(CH_2)_qNHR_a$ with an activated derivative of the appropriate acid $R_1{}^aCO_2H$ or $R_b{}'CO_2H$.

Compounds of formula (XIV) in which $D^a$ is aralkylidenaminoalkyl may be prepared from the corresponding amine by standard procedures.

Compounds of formula (I) can be produced by reacting a compound of formula (XIX)

R₁R₂NAlkQE      (XIX)

in which E represents $(CH_2)_nX(CH_2)_mP$ or CH₂P′ where P and P′ are leaving groups, with a triazole of the formula (XVI) where U represents amino, HS(CH₂)ₘNH or HO(CH₂)ₘNH, and R₄ is as defined in formula (I) or is a group convertible thereto.

Thus for example compounds of formula (I) may be prepared by reacting a compound of formula (XIX) in which E represents $(CH_2)_nX(CH_2)_mP$ and P represents a leaving group such as halogen, e.g. chlorine or bromine, or sulphonyloxy, e.g. mesyloxy or tosyloxy with the triazole (XVI) in which U represents an amino group, the reaction being carried out in a suitable solvent such as dimethylformamide or acetonitrile.

Compounds of formula (I) may also be prepared by introducing the group R₁R₂NAlk— into the group Q present in a suitable intermediate or converting another group already present into a group R₁R₂NAlk. Thus compounds of formula (I) in which Alk represents a methylene group and Q represents a furan or substituted furan ring as defined in formula (I) may be prepared from a compound of formula (XX)

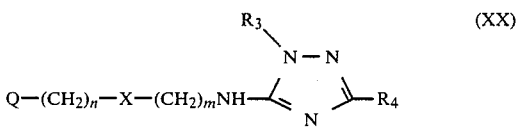

Q—(CH₂)ₙ—X—(CH₂)ₘNH—⟨N-N⟩—R₄      (XX)

in which Q represents a furan or substituted furan ring as defined in formula (I), by means of a Mannich reaction wth formaldehyde and an amine R₁R₂NH or a salt thereof. The reaction may be carried out by reacting the amine salt with aqueous formaldehyde and the compound (XX) or by refluxing the amine salt with paraformaldehyde and compound (XX) in a suitable solvent such as ethanol.

Compounds of formula (I) in which R₁ and R₂ are both methyl, Alk is methylene and Q represents a thiophen ring, a furan ring or a substituted furan ring as defined in formula (I) may be prepared from compound (XX) in which Q may additionally represent a thiophen ring, by reaction with a compound (CH₃)₂N⊕=CH₂Cl⊖ in a solvent such as acetonitrile at an elevated temperature, e.g. reflux. The compounds of formula (XX) may be prepared by methods analogous to those already described for the compounds of formula (I).

Compounds of formula (I) in which R₄ is a secondary or tertiary hydroxyalkyl group may be prepared by treating the corresponding compound where R₄ is the group $(CH_2)_{q-1}CHO$, $(CH_2)_{q-1}CO_2R_7$ or $(CH_2)_rCOR_7$ in which q,r and R₇ as defined previously with an organometallic derivative such as a Grignard reagent, e.g. a C₁₋₅alkyl magnesium halide or an organolithium, e.g. alkyl lithium reagent in a suitable solvent such as diethyl ether or tetrahydrofuran.

Intermediates in preparing the compounds of formula (I) wherein R₄ is a group convertible into R₄ as defined in formula (I) include aldehydes, ketones, esters, amides and nitriles. Such intermediates may be prepared by methods analogous to those already described for preparing compounds of formula (I).

Compounds of formula (I) may be prepared by reacting a compound of formula (XXI)

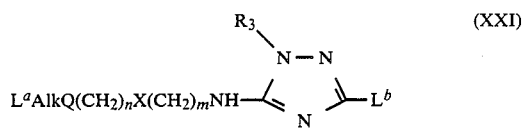

$L^aAlkQ(CH_2)_nX(CH_2)_mNH$—⟨N-N⟩—$L^b$      (XXI)

where either $L^a$ is R₁R₂N and $L^b$ is the group $(CH_2)_qL^c$ or $L^a$ is a group $L^d$ and $L^b$ is R₄ where $L^c$ and $L^d$ are leaving groups, with a compound capable of replacing $L^a$ by R₁R₂N or $L^c$ so as to convert $L^b$ into the group R₄. Examples of the leaving group $L^d$ include halogen, e.g. chlorine or bromine, or quaternary ammonium, e.g. trimethylammonium and examples of the leaving group $L^c$ include halogen, e.g. chlorine or bromine.

The leaving group $L^d$ may be displaced by treatment with an amine R₁R₂NH to give a compound of formula (I). The leaving group $L^c$ may be displaced by treating the compound of formula (XXI) with either ammonia or a primary or secondary amine to give a compound of formula (I) in which R₄ is an aminoalkyl, alkylaminoalkyl or dialkylaminoalkyl group or with the anion of an appropriate alcohol or phenol, e.g. with alkoxide, to give a compound of formula (I) in which R₄ is an ether group, e.g. alkoxyalkyl.

The displacement of halide ions with ammonia or an amine may be carried out in the absence or presence of a solvent such as acetonitrile. Displacement with the anion of an appropriate alcohol or phenol may be effected by treatment with a suitable alkali metal derivative, e.g. sodium methoxide, in a suitable solvent e.g. dimethylformamide, or the alcohol corresponding to the anion. Displacement of a quaternary ammonium group may be effected by heating with an excess of the appropriate amine.

Compounds of formula (I) in which $R_4$ has a particular meaning may be converted into other compounds of the invention by standard methods of interconversion.

Thus a compound in which $R_4$ is an alkoxyalkyl group may be prepared by treating a corresponding compound of formula (I) in which $R_4$ is a hydroxyalkyl group with for example an alkyl halide in a suitable solvent such as dimethylformamide in the presence of a base e.g. sodium hydride.

According to a further possibility alkylation (e.g. methylation) of a compound in which $R_4$ is a primary or secondary aminoalkyl group may be effected by treatment with formaldehyde and formic acid (the Eschweiler-Clarke procedure).

Compounds of formula (I) in which $R_4$ is an acyloxyalkyl group may be prepared by treating the corresponding hydroxyalkyl compound with an appropriate acid, e.g. acetic or benzoic acid at elevated temperatures e.g. 80°–120° C. in the absence or presence of a solvent such as toluene.

Compounds of formula (I) in which $R_4$ is an alkenyl group may be prepared from the corresponding hydroxyalkyl compound by heating with an acid, e.g. toluene sulphonic acid, in a suitable solvent, e.g. acetonitrile.

Compounds of formula (I) in which $R_4$ represents a hydroxyalkyl group may be prepared by removal of a suitable hydroxyl protecting group. Examples of such protected hydroxyl groups include ethers, such as trialkylsilyl e.g. trimethylsilyl, aralkyl such as benzyl, benzhydryl or trityl, tetrahydropyranyl or alkoxymethyl, e.g. methoxymethyl ethers, or esters of carboxylic acids such as alkanoic acids e.g. formic acid or acetic acid, or aromatic acids such as benzoic acid, or aralkanoic acids e.g. phenylacetic acid or haloalkanoic acids such as trifluoroacetic acid or trichloropropionic acid.

The protecting groups may be removed by conventional procedures c.f. Protective Groups in Organic Chemistry 1973 edited by J. F. W. McOmie. For example benzyl and benzhydryl ether groups may be removed by catalytic hydrogenolysis with for example hydrogen and a palladium catalyst; the trityl, tetrahydropyranyl, alkoxymethyl and trialkylsilyl ether groups may be removed by acid hydrolysis. The esters may be cleaved by acid or alkaline hydrolysis.

The diazonium salts (III), the aminoguanidines (XIII) and the compounds of formula (XIX) in which E represents $(CH_2)_nX(CH_2)_mP$ may be prepared as described in British Patent Specification No. 2023133A.

Where the product of any of the above processes is a free base and a salt is required, the salt may be formed in a conventional manner. Thus for example, a generally convenient method of forming the salts is to mix appropriate quantities of the free base and the acid in an appropriate solvent(s) e.g. an alcohol such as ethanol or an ester such as ethyl acetate.

The invention is illustrated but not limited by the following preparations and Examples. In the following examples temperatures are in °C. "T.l.c." refers to thin layer chromatography carried out on silica using, unless otherwise stated, one of the following solvent systems:
System A: methanol: 0.88 ammonia (79.1)
System B: ethyl acetate:water:isopropanol:0.88 ammonia (25:8:15:2)
System C: ethyl acetate:ethanol:0.88 ammonia (20:3:2).
Preparative chromatography was carried out on silica using methanol as eluant unless otherwise stated.

PREPARATION 1

(a) 4-[3-(1-piperidinylmethyl)phenoxy]butanal

4-[3-(1-piperidinylmethyl)phenoxy]butannitrile

A mixture of sodium hydride (1.5 g) and 3-(1-piperidinylmethyl)phenol (11.2 g) in dimethylformamide (60 ml) was stirred at room temperature for 5 h. 4-Bromobutannitrile (9.0 g) was added, and stirring was continued for a further 24 h. The mixture was poured onto ice and extracted with ethyl acetate which was washed with water and brine, and distilled to give the title compound as a colourless oil (14.78 g) b.p. 200°, 0.08 mm; tlc system A $R_f$ 0.8.

4-[3-(1-piperidinylmethyl)phenoxy]butanal semicarbazone

A solution of 4-[3-(1-piperidinylmethyl)phenoxy]butannitrile (51.6 g) sodium acetate (73.8 g) and semicarbazide hydrochloride (77.6 g) in 50% aqueous ethanol (1 L) was hydrogenated over Raney Nickel (50 g). The catalyst was removed by filtration. The filtrate was partially evaporated, made basic with potassium carbonate and extracted with ethyl acetate. The organic extract was evaporated to leave an oil which was purified by column chromatography to give the title compound as a pale yellow oil (48.6 g); tlc System B, $R_f$ 0.8.
N.M.R. (CDCl$_3$) 0.28, brs, (1H); 2.6,s, (1H); 2.9,t, (1H); 3–3.4,m,(3H); 4.4, brs, (2H); 6.02,t, (2H);6.57,s, (2H); 7.4–7.8,m, (4H); 7.95, m, (2H); 8.2–8.9,m, (8H).

4-[3-(1-piperidinylmethyl)phenoxy]butanal

4-[3-(1-piperidinylmethyl)phenoxy]butanal semicarbazone (9.43 g) and 37% formaldehyde (80 ml) in 2N hydrochloric acid (80 ml) were stirred at room temperature for 2.5 h and then diluted with water. The solution was basified with sodium carbonate and extracted with ether. The organic extract was washed with brine, and distilled to give the title compound as a colourless oil (5.59 g) b.p. 200°, 0.06 mm; tlc methanol $R_f$ 0.7.

(b) Similarly prepared from 3-[(dimethylamino)methyl]phenol (12.08 g) was 4-[3-[(dimethylamino)methyl]phenoxy]butanal (1.05 g) as a colourless oil b.p. 150°, 0.06 mm; tlc System A, $R_f$ 0.59.

PREPARATION 2

4-[3-(1-piperidinylmethyl)phenoxy]butanoic acid

Ethyl 4-[3-(1-piperidinylmethyl)phenoxy]butanoate

A mixture of 3-(1-piperidinylmethyl)phenol (11.2 g) sodium hydride (1.5 g) and ethyl 4-bromobutyrate (11.7 g) in dimethylformamide (60 ml) was stirred at 25° during 20 h. The mixture was poured onto ice (300 g) and extracted with ethyl acetate (3 × 100 ml). The combined extracts were distilled to give the title compound as a colourless oil (16.9 g) b.p. 250°, 0.1 mm; tlc System B, $R_f$ 0.9.

4-[3-(1-piperidinylmethyl)phenoxy]butanoic acid

A solution of ethyl-4-[3-(1-piperidinylmethyl)phenoxy]butanoate (6.1 g) and potassium hydroxide (6.0 g) in ethanol (50 ml) and water (50 ml) was heated under reflux during 0.5 h. The cool solution was neutralised to pH 7 with 5N hydrochloric acid, and evaporated to dryness under reduced pressure. The residue was dissolved in ethanol (100 ml), filtered and the filtrate was evaporated to leave a residue which was crystallised from a mixture of methanol and ether to give the title compound as a white crystalline solid (4.91 g) m.p. 73.5°; tlc System B, R$_f$ 0.3.

Preparation 3

Methyl 5-amino-1-methyl-1H-1,2,4-triazole-3-carboxylate

A stirred suspension of 5-amino-1-methyl-1H-1,2,4-triazole-3-carboxylic acid (9.10 g) in methanol (100 ml) was saturated with dry hydrogen chloride, and heated under reflux for 4.5 h. The cooled solution was partially evaporated, diluted with water (100 ml) and the pH was adjusted to pH 7 with potassium carbonate. The solution was filtered, and the filtrate partially evaporated to give the title compound as a white solid (4.60 g) m.p. 190–1; tlc System B, R$_f$ 0.6.

PREPARATION 4

3-[3-(1-piperidinylmethyl)phenoxy]propanoic acid

3-[3-(1-piperidinylmethyl)phenoxy]propannitrile

A solution of 3-(1-piperidinylmethyl)phenol (26 g), acrylonitrile (100 ml) and benzyltrimethylammonium hydroxide (40% methanolic solution, 5 ml) was heated at reflux for 40 h. The mixture was evaporated in vacuo, diluted with ether (300 ml) and filtered. The filtrate was washed with 2N sodium hydroxide, water and distilled to give the title compound as a colourless oil (17.5 g) b.p. 170°, 0.07 mm; tlc system B, R$_f$ 0.8.

3-[3-(1-piperidinylmethyl)phenoxy]propionic acid

A solution of 3-[3-(1-piperidinylmethyl)phenoxy]propannitrile (1.5 g) in 2N sulphuric acid (115 ml) was heated under reflux for 72 h. The pH of the cooled solution was adjusted to pH 7 and the suspension was treated with ethanol, filtered and evaporated to dryness. The resulting residue was extracted with hot ethanol. Ether was added to the cooled extract to give the title compound as a white solid (12 g) m.p.178.5°–179.5°; tlc System B, R$_f$ 0.4.

PREPARATION 5

(a) Methyl N-[2-(acetyloxy)acetyl]-1-methyl-2-(phenylmethylene)-hydrazinecarboximidothioate Methyl 1-methyl-2-(phenylmethylene)hydrazinecarboximidothioate hydroiodide A mixture of dimethyl dithiocarbamate hydroiodide (10 g) and 1-methyl-2-(phenylmethylene)hydrazine (5.4 g) was heated at 60° under water pump pressure for 1 h. The residue was triturated with hot ethyl acetate (20 ml) to give the title compound (13.3 g) as a yellow solid, m.p.183.4° tlc System A R$_f$ 0.75.

Methyl N-[2-(acetyloxy)acetyl]-1-methyl-2-(phenylmethylene)-hydrazinecarboximidothioate Methyl 1-methyl-2-(phenylmethylene)hydrazinecarboximidothioate, hydroiodide (1.34 g) was dissolved in saturated potassium carbonate solution and extracted with ether. The combined organic extracts were dried and evaporated to give an off-white solid which was dissolved in acetone (25 ml) and treated with potassium carbonate (1.1 g) followed by (acetyloxy)acetyl chloride (0.85 g). The suspension was stirred at room temperature for 2 h and evaporated in vacuo. The residue was suspended in water (50 ml) and filtered to give the title compound (1.01 g) which was recrystallised from ethanol, m.p. 115°–117°.

Found: C, 54.7; H; 5.6; N,13.4; C$_{14}$H$_{17}$N$_3$O$_3$S requires: C, 54.7; H; 5.6; N,13.7%.

The following compounds were similarly prepared from the corresponding methyl-1-alkyl-2-(phenylmethylene)hydrazinecarboximidothioate hydroiodide (A) and the corresponding acid chloride.

(b) A (3.4 g) and phenyl acetyl chloride (1.6 g) gave methyl-1-methyl-N-phenylacetyl-2-(phenylmethylene)-hydrazinecarboximidothioate (1.3 g) m.p. 147°–8°.

tlc. silica; ethyl acetate R$_f$ 0.75.

PREPARATION 6

Following the method of Preparation 5, methyl 1-methyl-2-(phenylmethylene)hydrazinecarboximidothioate (20 g) and ethyl malonyl chloride (12 g) gave ethyl 3-[[[1-methyl-2-(phenylmethylene)hydrazino](methylthio)methylene]amino]-3-oxopropanoate (5.6 g) m.p. 74°–5°.

N.m.r. (CDCl$_3$) 2.2,s,(1H); 2.2–2.4,m,(2H); 2.5–2.7,m,(3H); 5.82,q,(2H); 6.49,s,(2H); 6.52,s,(3H) 7.6,s,(3H) 8.73,t,(3H).

PREPARATION 7

The following compound was prepared using the method of Example 16;

3-[3-(1-piperidinylmethyl)phenoxy]propananamine (3.61 g) and ethyl 3-[[[1-methyl-2-(phenylmethylene)-hydrazino](methylthio)methylene]amino]-3-oxopropanoate (4.7 g) gave ethyl 3-[[[1-methyl-2-(phenylmethylene)hydrazino][[3-[3-(1-piperidinylmethyl)phenoxy]propyl]amino]methylene]amino]-3-oxopropanoate (7.3 g).

Nmr. (CDCl$_3$) 2.1,br, (1H); 2.23,s, (1H); 2.3–2.5,m,(2H); 2.55–2.7,m,(3H); 2,83,t, (1H), 3–3.3,m,(3H); 5.8,q,(2H) 5.9,t, (2H); 6.4,m,(2H); 6.53,2,(3H); 6.55,s,(2H); 6.68,s, (2H); 7.5–8,m, (6H); 8.5,m,(6H); 8.7,t,(3H); t.l.c. System A Rf 0.65.

The above ethyl ester (1.84 g) was acidified to give ethyl 1-methyl-5-[[3-[3-(1-piperidinylmethyl)phenoxy]-propyl]amino]-1H-1,2,4-triazole-3-acetate (0.5 g) N.m.r. (CDCl$_3$) 2.77,t, (1H); 3–3.3,m, (3H); 5.4,t,(1H); 5.8,q,(2H); 5.9,t,(2H) 6.3–6.6,3xs+q, (9H); 7.6,m, (4H); 8.5,m,(6H), 8.2,t,(3H); T.l.c. System A Rf 0.63.

PREPARATION 8

5-[[3-(3-Formylphenoxy)propyl]amino]-1-methyl-1H-1,2,4-triazole-3-methanol

N'-[2-(Acetyloxy)acetyl]-N'-[3-[3-(1,3-dioxolan-2-yl)phenoxy]propyl]-1-methyl-2-(phenylmethylene)-hydrazinecarboximidamide A mixture of 3-[3-(1,3-dioxolan-2-yl)phenoxy]-propanamine (2.9 g) and methyl-N-[2-(acetyloxy)acetyl]-1-methyl-2-(phenylmethylene)hydrazinecarboximidothioate (4 g) was heated at 60° under water pump vacuum for 3 h to give a glass which was triturated with ether to give the title compound as a white solid (5.39 g) m.p. 78°–80° t.l.c. silica methanol Rf 0.8.

5-[[3-(3-Formylphenoxy)propyl]amino]-1-methyl-1H-1,2,4-triazole-3-methanol

A suspension of N'-[2-(acetyloxy)acetyl]-N'-[3-[3-(1,3-dioxolan-2-yl)phenoxy]propyl]-1-methyl-2-(phenylmethylene)hydrazinecarboximidamide (5 g) in 2N hydrochloric acid (100 ml) and ethanol (25 ml) was stirred at room temperature for 16 h. The solution was neutralised to pH 7 with potassium carbonate, treated with potassium hydroxide (1.7 g), diluted with ethanol (50 ml) and stirred for a further 15 min. The pH of the solution was adjusted to pH 7 with 2N hydrochloric acid, and the solvent was partially evaporated to leave an aqueous solution which was extracted with ethyl acetate. The combined organic extracts were dried and evaporated to give the title compound as a foam (2.63 g) t.l.c. silica, ethyl acetate: methanol; 2:1 Rf 0.5, nmr (CDCl$_3$) 0.00, s, (1H); 2.5-2.9,m, (4H); 5.4, t, (1H); 6.4, q, (2H); 6.50, s, (3H); 7.85,m, (2H).

EXAMPLE 1

(a)

3-methyl-N-[3-[3-(N,N-dimethylaminomethyl)phenoxy]propyl]-H-1,2,4-triazole-5-amine A mixture of 3-(3-aminopropoxy)-N,N-dimethylbenzenemethanamine (A) (2.0 g) and methylisothio semicarbazide hydroiodide (2.24 g) was heated at 40° for 6 h. The residual gum was dissolved in ethanol and treated with a solution of tartaric acid in ethyl acetate. The solid that precipitated was filtered off and heated under reflux in glacial acetic acid (15 ml) for 4 h. The mixture was cooled, basified with potassium carbonate and extracted with ether. The organic extract was purified by column chromatography to give the title compound after recrystallisation from a mixture of ethyl acetate and light petroleum (b.p. 60°-80°) as a buff solid (0.8 g) m.p. 133°-133.5°. tlc System A,R$_f$0.58.

The following were similarly prepared from the appropriate acid, the appropriate diamine and methylisothiosemicarbazide hydroiodide (B).

(b) Diamine A (1.46 g), B (2.75 g) and phenyl acetic acid (3.0 g), carrying out the reaction with the acid in refluxing ethanol (50 ml) for 72 hr., gave 3-phenylmethyl-N-[3-[3-[(dimethylamino)methyl]phenoxy]propyl]-1H-1,2,4-triazole-5-amine (0.06 g) m.p. 140°-141°. tlc System A,R$_f$0.49

(c) Dimaine A (1.46 g), B (1.73 g) and benzoic acid (5.0 g), carrying out the reaction with the acid by heating at 140° for 12 hr., gave 3-phenyl-N-[3-[3-[(dimethylamino)methyl]phenoxy]propyl]-1H-1,2,4-triazole-5-amine (0.62 g) m.p. 126.5°-127.5° tlc System A,R$_f$ 0.48.

(d) 3-[3-(1-piperidinylmethyl)phenoxy]propanamine (4.96 g), B(4.94 g) and phenyl acetic acid (8.16 g), carrying out the reaction with the acid in refluxing toluene (20 ml) for 6 hr., gave 3-phenylmethyl-N-[3-[3-(1-piperidinylmethyl)phenoxy]propyl]-1H-1,2,4-triazole-5-amine (1.3 g) m.p. 143°-4° tlc System A,R$_f$0.5.

EXAMPLE 2

(a)

1-methyl-N-[3-[3-(N,N-dimethylaminomethyl)phenoxy]propyl]-1H-1,2,4-triazole-5-amine A solution of sodium nitrite (1.74 g) in water (15 ml) was added dropwise to a solution of 1-methyl-N$^5$-[3-[3-(N,N-dimethylaminomethyl)phenoxy]propyl]-1H-1,2,4-triazole-3,5-diamine (5 g) in concentrated sulphuric acid (3.68 g) and ethanol (200 ml). The reaction mixture was heated at 65° for 4 h, cooled, treated with saturated brine (100 ml) and extracted with ethyl acetate. Evaporation of the organic extract gave a red oil which was extracted with ether. Distillation of the ether extracts gave the title compound as a pale yellow oil (1.8 g) b.p. 190° (0.04 mm). tlc System A,R$_g$ 0.6.

The following compounds were similarly prepared:

(b) 1-methyl-N$^5$-[3-[3-(1-piperidinylmethyl)phenoxy]propyl]-1H-1,2,4-triazole-3,5-diamine (1.72 g) gave 1-methyl-N-[3-[3-(1-piperidinylmethyl)phenoxy]propyl]-1H-1,2,4-triazole-5-amine (1.25 g) as a yellow oil; b.p. 220°, 0.08 mm; tlc System B, R$_f$0.5.

(c) 1-methyl-N$^5$-[3-[3-[(hexamethyleneiminyl)methyl]phenoxy]propyl]-1H-1,2,4-triazole-3,5-diamine (1.79 g) gave 1-methyl-N-[3-[3-[(hexamethyleneiminyl)methyl]phenoxy]propyl]-1H-1,2,4-triazole-5-amine (500 mg) b.p. 240° 0.15 mm; tlc System B, R$_f$0.75.

EXAMPLE 3

(a)

3-chloro-1-methyl-N-[3-[3-(N,N-dimethylaminomethyl phenoxy]propyl]-1H-1,2,4-triazole-5-amine A solution of sodium nitrite (0.46 g) in water (1.5 ml) was added dropwise to a solution of 1-methyl-N$^5$-[3-[3-(N,N-dimethylaminomethyl)phenoxy]propyl]-1H-1,2,4-triazole-3,5-diamine (2.0 g) in concentrated hydrochloric acid at 5°. This solution of the diazonium salt was added to a solution of cuprous chloride at 75° [prepared by adding a solution of sodium metabisulphite (0.41 g) and sodium hydroxide (0.27 g) in water (3 ml) to a hot solution of copper sulphate (1.89 g) and sodium chloride (1.61 g) in water (6 ml)].

Concentrated hydrochloric acid (84 ml) was added to the reaction mixture which was allowed to stand at 25° for 12 h, cooled, basified with sodium bicarbonate and extracted with ethyl acetate. Distillation of the organic extract gave the title compound as a pale yellow oil (1.23 g) b.p. 225° (0.04 mm). tlc System A,R$_f$0.64.

(b) Similarly prepared from 1-methyl-N$^5$-[3-[3-(1-piperidinylmethyl)phenoxy]propyl]-1H-1,2,4-triazole-3,5-diamine (11.3 g) was 3-chloro-1-methyl-N-[3-[3-(1-piperidinylmethyl)phenoxy]propyl]-1H-1,2,4-triazole-5-amine (3.05 g) b.p. 250°, 0.06 mm, tlc System B,R$_f$0.8.

EXAMPLE 4

(a)

N-[4-[3-[(dimethylamino)methyl]phenoxy]butyl]-3-phenylmethyl-1H-1,2,4-triazole-5-amine A solution of 4-[3-[(dimethylamino)methyl]phenoxy]butanal (0.5 g) and 3-phenyl methyl-1H-1,2,4-triazole-5-amine (0.39 g) in dry toluene (60 ml) was heated under reflux during 3 h. The solvent was evaporated and replaced with methanol (50 ml). Sodium borohydride (0.4 g) was added and the mixture was stirred at 20° during 2 h. The methanol was evaporated and the residue partitioned between water and ethyl acetate. The organic extract was evaporated and the residue was purified by column chromatography to give the title compound, which crystallised from a mixture of ethyl acetate and cyclohexane as pale yellow crystals (0.09 g) m.p. 131°-3°; tlc system A,R$_f$0.6.

The following compounds were similarly prepared from the appropriate aldehyde and aminotriazole:

(b) 4-[3-(1-piperidinylmethyl)phenoxy]butanal (0.4 g), 3-methyl-1H-1,2,4-triazole-5-amine (0.15 g) and sodium borohydride (0.4 g) gave 3-methyl-N-[4-[3-(1-piperidinylmethyl)phenoxy]butyl]-1H-1,2,4-triazole-5-amine (50 mg) m.p. 138°-9°; tlc System A, R$_f$0.64

(c) 4-[3-(1-piperidinylmethyl)phenoxy]butanal (0.5 g) 3-phenylmethyl-1H-1,2,4-triazole-5-amine (0.33 g) and sodium borohydride (0.4 g) gave 3-phenylmethyl-N-[4-[3-(1-piperidinylmethyl)phenoxy]butyl]-1H-1,2,4-triazole-5-amine (0.16 g) m.p. 145°-6° tlc. System A, R$_f$ 0.6.

EXAMPLE 5

(a)
3-(2-phenylethyl)-N-[4-[3-(1-piperidinylmethyl)phenoxy]butyl]-1H-1,2,4-triazole-5-amine N-[3-(2-phenylethyl)-1H-1,2,4-triazol-5-yl]-4[3-(piperidinylmethyl)phenoxy]butanamide A solution of 4-[3-(1-piperidinylmethyl)phenoxy]-butanoic acid (1.0 g), thionyl chloride (1.29 g) and dimethylformamide (6 drops) in methylene chloride (50 ml) was stirred at 25° during 5 h. The solvent was evaporated and the residue was dissolved in methylene chloride (50 ml). 3-phenylethyl-1H-1,2,4-triazole-5-amine (0.68 g) was added and the mixture was stirred at 25° during 12 h. The solvent was removed and the residue was diluted with water (50 ml). The pH of the aqueous solution was adjusted to pH 8 with sodium bicarbonate and extracted with ethyl acetate. The combined organic extracts were evaporated and the residue was heated at 155° during 2 h. The resulting solid was triturated under hot methanol to give the title compound (0.5 g) as a white powder m.p. 192°–3° tlc System A,$R_f$ 0.62.

3-(2-phenylethyl)-N-[4-[3-(1-piperidinylmethyl)phenoxy]butyl]-1H-1,2,4-triazole-5-amine A suspension of N-[3-(2-phenylethyl)-1H-1,2,4-triazol-5yl]-4-[3-(1-piperidinylmethyl)phenoxy]butanamide (0.4 g) and lithium aluminium hydride (0.33 g) in dioxan (50 ml) was heated under reflux in a nitrogen atmosphere during 12 h. The cool mixture was quenched with water (50 ml) and extracted with ethyl acetate. The combined organic extracts were evaporated and the residue was crystallized from ethyl acetate to give the title compound as a white solid (0.23 g) m.p. 146°–7° tlc System A, $R_f$ 0.71.

The following compounds were similarly prepared from 4-[3-(1-piperidinylmethyl)phenoxy]butanoic acid (A) and the corresponding triazoles:

(b) A (1.0 g) and 3-methylthio-1H-1,2,4-triazole-5-amine (0.47 g) gave 3-methylthio-N-[4-[3-(1-piperidinylmethyl)phenoxy]butyl]-1H-1,2,4-triazole-5-amine (0.1 g), m.p. 122°–3° tlc System a $R_f$ 0.73

(c) A (1.0 g) and 3-(2-methylpropyl)-1H-1,2,4-triazole-5-amine (0.68 g) gave 3-(2-methylpropyl)-N-[4-[3-(1-piperidinylmethyl)phenoxy]butyl]-1H-1,2,4-triazole-5-amine (0.08 g), m.p. 141°–142°.

N.m.r. (CDCl$_3$) 2.78,t,(1H); 3.0–3.3,m,(3H); 5.02, br, (1H); 6.0, m,(2H); 6.60, s+m, (4H); 7.2–8.8, m,(18H); 9.05,d,(6H).

EXAMPLE 6

5-[4-[3-(1-piperidinylmethyl)phenoxy]butyl]amino-1H-1,2,4-triazole-3-methanol

Ethyl 5-[4-[3-(1-piperidinylmethyl)phenoxy]butyl]amino-1H-1,2,4-triazole-3-carboxylate Methyl 5-amino-1H-1,2,4-triazole-3-carboxylate (0.568 g) and 4-[3-(1-piperidinylmethyl)phenoxy]butanal in ethanol (40 ml) were heated at reflux for 2 h. The cooled reaction mixture was treated with sodium borohydride (0.4 g) and stirred at room temperature for 15 h. The solvent was evaporated and the residue was dissolved in 2N hydrochloric acid which was washed with ethyl acetate, basified with sodium carbonate and extracted with ethyl acetate. The combined organic extracts were evaporated to yield the title compound as a white solid which was recrystallised from a mixture of ethyl acetate and ethanol (1:1) (0.5 g) m.p. 170°–1° dec.; tlc System B, $R_f$ 0.8.

5-[4-[3-(1-piperidinylmethyl)phenoxy]butyl]amino-1H-1,2,4-triazole-3-methanol

A mixture of ethyl 5-[4-[3-(1-piperidinylmethyl)phenoxy]butyl]amino-1H-1,2,4-triazole-3-carboxylate (0.3 g) and lithium aluminium hydride (0.1 g) in tetrahydrofuran (50 ml) was stirred at room temperature for 0.5 h, then quenched with water. The solid was filtered off and washed with methanol. The filtrate and washings were evaporated to leave a residue which was extracted with hot ethyl acetate. Evaporation of the extract gave an oil that solidified. It was crystallised from ethyl acetate to give the title compound as an off-white solid (0.094 g) m.p. 127°–8° dec. tlc System B, $R_f$ 0.7.

EXAMPLE 7

1-methyl-5-[[4-[3-(1-piperidinylmethyl)phenoxy]butyl]amino]-1H-1,2,4-triazole-3-methanol Methyl 1-methyl-5-[[1-oxo-4-[3-(1-piperidinylmethyl)phenoxy]butyl]amino]-1H-1,2,4-triazole-3-carboxylate A solution of 4-[3-(1-piperidinylmethyl)phenoxy]-butanoic acid (2.77 g), thionyl chloride (2.5 ml) and dimethylformamide (6 drops) in methylene chloride (80 ml) was stirred at room temperature for 2 h. The mixture was evaporated in vacuo. The resulting solid was dissolved in dimethylformamide (50 ml) and treated with methyl 5-amino-1-methyl-1H-1,2,4-triazole-3-carboxylate (1.56 g) After 18 h at room temperature, the mixture was evaporated in vacuo and the residue was dissolved in water. The combined organic extracts were washed with water and evaporated in vacuo. The resulting solid was recrystallised from a mixture of ethyl acetate and cyclohexane to yield the title compound as a white powder (2.0 g) m.p. 108°–10° tlc System B, $R_f$ 0.7.

1-Methyl-5-[[4-[3-(1-piperidinylmethyl)phenoxy]butyl]amino]-1H-1,2,4-triazole-3-methanol A suspension of methyl 1-methyl-5-[[1-oxo-4-[3-(1-piperidinylmethyl)phenoxy]butyl]amino]-1H-1,2,4-triazole-3-carboxylate (1.25 g) and lithium aluminium hydride (1.0 g) in tetrahydrofuran (30 ml) was stirred under nitrogen at room temperature for 5 h, cooled to 0° and quenched with water. The mixture was diluted with ethyl acetate, filtered and the filtrate was evaporated in vacuo. The residue was chromatographed to give an oil, which crystallised on trituration with ether to yield the title compound as a white solid (0.33 g) m.p. 84°–5°, tlc System B,$R_f$ 0.6.

EXAMPLE 8

1-methyl-5-[[3-[3-(1-piperidinylmethyl)phenoxy]propyl]amino]-1H-1,2,4-triazole-3-methanol A stirred suspension of 3-[3-(1-piperidinylmethyl)-phenoxy]propanoic acid (1.84 g) in methylene chloride (50 ml) and dimethylformamide (5 drops) was treated with thionyl chloride (2.0 ml). The solution was maintained for 2 h at room temperature and then evaporated in vacuo. The oily product was dissolved in dimethylformamide (50 ml) and treated with methyl-5-amino-1-methyl-1H-1,2,4-triazole-3-carboxylate (1.09 g). The reaction mixture was stirred at room temperature for 16 h, evaporated in vacuo, the residue was dissolved in 8% sodium bicarbonate solution and washed with ethyl acetate. The organic extracts were washed with water and evaporated in vacuo to give methyl 1-methyl-5-[[1-oxo-4-[3-(1-piperidinylmethyl)phenoxy]propyl]amino]-1H-1,2,4-triazole-3-carboxylate as an oil (0.832 g) which was dissolved in tetrahydrofuran (30 ml) and treated with lithium aluminium hydride (0.6 g) at 0°. The mixture was stirred at room temperature for 6 h, then quenched with water, diluted with ethyl acetate and filtered. The filtrate was evaporated in vacuo to yield an oil (0.586 g), which was purified by column chromatography to give an oil, which crystallised on trituration with ether to yield the title compound (0.136 mg) as a white solid m.p. 118°–9° tlc System B, $R_f$ 0.7.

EXAMPLE 9

5-[[3-[3-(1-piperidinylmethyl)phenoxy]propyl]amino]-1H-1,2,4-triazole-3-one

A solution of 3-[3-(1-piperidinylmethyl)phenoxy]-propanamine (1.76 g) in tetrahydrofuran (70 ml) was treated with dimethyl N-methoxycarbonylcarbonimidodithioate (1.27 g) at room temperature, and the mixture was stirred for 6 h. Hydrazine hydrate (2 g) was added, and the mixture was heated under reflux for 18 h. The solution was evaporated, and the residue was chromatographed to give the title compound (250 mg) as a colourless oil. tlc. System B, $R_f$ 0.5. Nmr ($D_2O$) 2.5,t, (1H); 2.8–3.0,m,(3H); 5.72,s,(1H); 5.8,t, (3H); 6.5,m, (2H); 6.65,t, (2H); 7.05,br.t, (2H); 7.7–8.6,m, (8H).

EXAMPLE 10

1-methyl-3-phenylmethyl-N-[3-[3-(1-piperidinylmethyl)phenoxy]propyl]-1H-1,2,4-triazole-5-amine, tartrate N-[[1-methyl-2-(phenylmethylene)hydrazino][[3-[3-(1-piperidinylmethyl)phenoxy]propyl]amino]methylene]-benzeneacetamide A mixture of 3-[3-(1-piperidinylmethyl)phenoxy]-propanamine (0.38 g) and methyl 1-methyl-N-phenylacetyl-2-(phenylmethylene)hydrazinecarboximidothioate (0.5 g) was heated at 50° under water pump vacuum during 4 h. The residue was dissolved in cyclohexane (20 ml) and light petroleum (b.p. 60°–80°) was added. The precipitate was removed by filtration and the filtrate was evaporated to give the title compound (0.65 g) as a colourless oil. tlc. System A $R_f$ 0.7.

N.m.r. (CDCl$_3$) 2.2–3.0,m, (12H); 3.0–3.3,m,(3H); 6.01,t, (2H); 6.30,s, (2H); 6.55,br.q, (2H); 6.62,s, (3H); 6.66,s (2H); 7.65,m, (4H); 8.00,m, (2H); 8.3–8.6,m,(6H).

1-methyl-3-phenylmethyl-N-[3-[3-(1-piperidinylmethyl)phenoxy]propyl]-1H-1,2,4-triazole-5-amine A solution of N-[[1-methyl-2-(phenylmethylene)hydrazino][[3-[3-[3-(1-piperidinylmethyl)phenoxy]propyl]amino]methylene]benzeneacetamide (0.65 g) in acetone (50 ml) was acidified to pH 1 with 2N hydrochloric acid and heated under reflux during 4 h. The solution was washed with ethyl acetate, basified with potassium carbonate and extracted with ethyl acetate. The combined organic extracts were dried and evaporated to give a residue which was purified by column chromatography. The resulting oil (0.4 g) was dissolved in ethyl acetate (10 ml), and a solution of tartaric acid (125 mg) in ethyl acetate (50 ml) was added to give the title compound (0.42 g) as a white powder.

tlc. System A, $R_f$ 0.65 N.m.r. (CDCl$_3$) (free base) 2.6–3.0,m,(6H); 3.0–3.4,m,(3H); 5.65,t, (1H); 5.95,t,(2H); 6.12,s,(2H); 6.47,q,(2H); 6.57,brs, (5H); 7.67,m, (4H); 7.93,m,(2H); 8.3–8.6,m, (6H).

EXAMPLE 11

5-[[2-[[[5-[(dimethylamino)methyl]-2-furanyl]methyl]-thio]ethyl]amino]-1-methyl-1H-1,2,4-triazole-3-methanol 2-(Acetyloxy)-N-[[[2-[[[5-[(dimethylamino)methyl]-2-furanyl]methyl]thio]ethyl]amino][1-methyl(2-phenylmethylene)hydrazino]methylene]acetamide A mixture of methyl N-[2-(acetyloxy)acetyl]-1-methyl-2-(phenylmethylene)hydrazinecarboximidothioate (0.92 g) and 5-[[(2-aminoethyl)thio]methyl]-N,N-dimethyl-2-furanmethanamine (0.64 g) in acetonitrile (5 ml) was stirred at room temperature for 3 h. The solution was evaporated in vacuo. The oily residue was suspended in ether (20 ml), filtered and the solid which crystallised was collected to give the title compound (0.8 g), m.p. 78°–80°.

tlc. System A $R_f$ 0.65.

5-[[2-[[[5-[(dimethylamino)methyl]-2-furanyl]methyl]thio]ethyl]amino]-1-methyl-1H-1,2,4-triazole-3-methanol A solution of 2-(acetyloxy)-N-[[[2-[[[5-[(dimethylamino)methyl]-2-furanyl]methyl]thio]ethyl]amino][1-methyl-2-(phenylmethylene)hydrazino]methylene]acetamide (0.74 g) in 2N hydrochloric acid was heated at 98°–100° for 1 h. Water (5 ml) was added to the cooled solution which was washed with ethyl acetate. The aqueous fraction was made alkaline with sodium carbonate and the solution was evaporated to dryness in vacuo. The residue was suspended in ethyl acetate (20 ml), excess anhydrous sodium carbonate and decolourising charcoal were added. The suspension was boiled for 10 mins, cooled, filtered and the filtrate was evaporated in vacuo. The residual oil was chromatographed on silica using methanol:0.88 ammonia, (79:1) to give the title compound (0.35 g) as a pale brown oil.

tlc. System A $R_f$ 0.6.

N.m.r. (CDCl$_3$) 3.92,s,(2H); 5.18,t,5.32,brs, 5.49,s, (4H); 6.33,s, (2H); 6.51,s,6.61,s+q,(7H); 7.23,t,(2H); 7.78,s,(6H).

EXAMPLE 12

1-methyl-5-[[4-[3-(1-piperidinylmethyl)phenoxy]butyl]amino]-1H-1,2,4-triazole-3-methanol acetate A solution of 1-methyl-5-[[4-[3-(1-piperidinylmethyl)phenoxy]butyl]amino]-1H-1,2,4-triazole-3-methanol (100 mg) in glacial acetic acid (5 ml) was heated under reflux for 8 h. The mixture was evaporated and the residue was triturated with ether to give the title compound as a white solid (97 mg) m.p. 119°–20°. tlc. System B,$R_f$ 0.8.

EXAMPLE 13

3-Methoxymethyl-1-methyl-5-[[4-[3-(1-piperidinylmethyl)phenoxy]butyl]amino]-1H-1,2,4-triazole A solution of 1-methyl-3-[[4-[3-(1-piperidinylmethyl)phenoxy]butyl]amino]-1H-1,2,4-triazole-3-methanol (149 mg) and thionyl chloride (3 ml) was stirred at room temperature for 0.5 h and evaporated. The residue was dissolved in methanol (5 ml) and added to a solution of sodium hydride (200 mg) in methanol (5 ml). The mixture was stirred at room temperature for 18 h, evaporated, and the residue was partitioned between ethyl acetate and water. The organic extracts were dried and evaporated to give an oil which was chromatographed on silica using ethyl acetate: isopropanol:water: 0.88 ammonia (25:15:8:2), to yield the title compound (108 mg).

tlc. System B, $R_f$ 0.6. N.M.R. (CDCl$_3$) 2.8,t,(1H); 3.0–3.3,m,(4H); 5.67,s,(2H); 5.72,t,(1H); 6.00,br.t, (2H); 6.3–6.6,m,(10H); 7.6,m,(4H); 8.0–8.7,m,(10H).

EXAMPLE 14

1,3-dimethyl-N-[4-[3-(1-piperidinylmethyl)phenoxy]-butyl]-1H-1,2,4-triazole-5-amine A stirred suspension of 4-[3-(1-piperidinylmethyl)-phenoxy]butanoic acid (4.0 g) in methylene chloride (100 ml) and dimethylformamide (24 drops) was treated with thionyl chloride (5.16 g). The solution was stirred at room temperature for 18 h and evaporated in vacuo, to give a pale yellow solid which was dissolved in methylene chloride (100 ml) and treated with 5-amino-1,3-dimethyl-1,2,4-triazole (1.61 g). The reaction mixture was stirred at room temperature for 24 h and evaporated in vacuo. The residue was dissolved in aqueous sodium bicarbonate solution and extracted with ethyl acetate. The organic extracts were dried and evaporated to give a brown oil which was dissolved in tetrahydrofuran (500 ml), treated with lithium aluminium hydride (3.04 g), stirred at room temperature for 18 h and refluxed for 3 h. The cooled reaction mixture was quenched with water (300 ml) and extracted with ethyl acetate. The combined extracts were washed with brine, dried and evaporated in vacuo to give an oil which was distilled to give the title compound (1.7 g) as a pale yellow oil, b.p. 230°/0.06 mm.

N.m.r. 2.80,t, (1H); 3.0–3.3,m, (3H); 5.82,t,(1H) 6.02,m, (2H); 6.58,s,s+m, (7H); 7.65,7.77m,s(7H) 8.0–8.7,m, (10H).

EXAMPLE 15

The following compounds were prepared using the method of Example 2:

1-methyl-N$^5$-[2-[[[5-[(dimethylamino)methyl]-2-furanyl]methyl]thio]ethyl]-1H-1,2,4-triazole-3,5-diamine (1.0 g) gave 1-methyl-N-[2-[[[5-[(dimethylamino)methyl]-2-furanyl]methyl]thio]ethyl]-1H,1,2,4-triazole-5-amine (0.32 g).

T.l.c. System C $R_f$ 0.54.N.m.r. (CDCl$_3$); 2.50,s,(1H); 3.90,s,(2H); 6.30,s,(2H); 6.5,2s+q, (7H); 7.18,t,(2H) 7.79,s,(6H).

(b) 1-methyl-N$^5$-[2-[[[5-[(dimethylamino)methyl]-2-thienyl]methyl]thio]ethyl]-1H-1,2,4-triazole-3,5-diamine (1.0 g) gave 1-methyl-N-[2-[[[5-[(dimethylamino)methyl]-2-thienyl]methyl]thio]ethyl]-1H-1,2,4-triazole-5-amine (0.31 g).

T.l.c. System C $R_f$ 0.52.N.m.r. (CDCl$_3$): 2.57,s,(1H); 3.3,m,(2H); 5.58,br,s,(1H); 6.16,s,(2H); 6.48,2s+q,(7H); 7.20,m, (2H); 7.76,s,(6H).

EXAMPLE 16

1-methyl-N-[[3-[3-(1-piperidinylmethyl)phenoxy]-propyl]amino]-1H-1,2,4-triazole-3-ethanol tartrate salt A suspension of ethyl 1-methyl-5-[[3-[3-(1-piperidinylmethyl)phenoxy]propyl]amino]-1H-1,2,4-triazole-3-acetate (0.3 g) and lithium aluminium hydride (100 mg) in tetrahydrofuran (50 ml) was stirred at 25° under nitrogen during 24 h. The mixture was quenched with water and extracted with ethyl acetate. The combined organic extracts were evaporated and the residue was chromatographed to give a pale yellow oil which dissolved in boiling cyclohexane. The hot solution was allowed to cool to room temperature, and the oil that precipitated was treated with a saturated solution of (d)-tartaric acid in ethyl acetate to give the title compound as a white powder (80 mg).

N.m.r. (free base) (CDCl$_3$); 2.8,t,(1H); 3–3.3,m,(3H); 5.3,t,(1H); 5.9,t, (2H); 6.13,t,(2H); 6.0,br,s,(1H) 6.4,q,(2H); 6.52,s,(3H) 6.57,s,(2H); 7.2,t,(2H); 7.65,m,(4H); 7.88,m,(2H); 8.5,m,(6H). T.l.c. System A $R_f$ 0.55.

EXAMPLE 17

(a)

5-[2-[[[5-[(dimethylamino)methyl]-2-thienyl]methyl]thio]ethyl]-1-methyl-3-phenylmethyl-1H-1,2,4-triazole-5-amine 2-(phenyl)-N[[[2-[[[5-[(dimethylamino)methyl]-2-thienyl]methyl]thio]ethyl]amino][1-methyl-2-(phenylmethylene)hydrazino]methylene]acetamide A mixture of 5-[[[2-(amino)ethyl]thio]methyl]-N,N-dimethyl-2-thiophene methanamine(C) (1.0 g) and methyl 1-methyl N-phenylacetyl-2-(phenylmethylene)-hydrazinecarboximidothioate (A) (1.42 g) was heated at 60° under water-pump vacuum during 3 h. to give the title compound (1.9 g) as a colourless oil.

T.l.c. System A $R_f$ 0.61.

N.m.r. (CDCl$_3$): 2.1,br,m, (1H); 2.2–2.4m (3H); 2.5–2.85,m,(8H); 3.3,dd (2H); 6.18,s,(2H); 6.33,s,(2H). 6.48,s,(2H); 6.68–6.70,m,(5); 7.4,t,(2H); 7.78,s,(6H).

5-[2-[[[5-[(dimethylamino)methyl]-2-thienyl]methyl]thio]ethyl]-1-methyl-3-phenylmethyl-1H-1,2,4-triazole-5-amine 2N hydrochloric acid (5 ml) was added to a solution of 2-(phenyl)-N-[[[2-[[[5-[(dimethylamino)methyl]-2-thienyl]methyl]thio]ethyl]amino][1-methyl-2-(phenylmethylene)hydrazino]methylene]acetamide (1.9 g) in toluene (20 ml) and the mixture was heated on a steam bath for 30 min. The aqueous layer was washed with toluene, treated with potassium carbonate, and evaporated in vacuo. The residue was dissolved in ethyl acetate, filtered and the filtrate was evaporated to yield an oil which was chromatographed to give the title compound (0.47 g) as a pale orange oil.

T.l.c. System A. $R_f$ 0.55.

Found C, 60.0; H, 6.8; N, 17.1; C$_{20}$H$_{27}$N$_5$S$_2$ requires: C, 59.8; H, 6.8; N, 17.4%.

The following compounds were similarly prepared from the appropriate methyl 1-methyl N-acyl-2-(phenylmethylene)hydrazinecarboximidothioate and the corresponding diamine (b) A (0.5 g) and 5[[(2-aminoethyl)thio]methyl]-N,N-dimethyl-2-furanmethanamine (0.33 g) gave 5-[2-[[[5-[(dimethylamino)methyl]-2-furanyl]methyl]thio]ethyl]-1-methyl-3-phenylmethyl-1H-1,2,4-triazole-5-amine (0.21 g).

T.l.c. System A $R_f$ 0.51.

N.m.r. (CDCl$_3$): 2.6–2.8,m,(5H); 3.95,s,(2H); 5.60,t,(1H); 6.12,s,(2H); 6.32,s,(2H); 6.55–6.63,m,(7H); 7.25,t,(2H); 7.79,s,(6H).

(c) A (1.21 g) and 5-[[(2-aminoethyl)thio]methyl]-3-N,N-trimethyl-2-furanmethanamine (0.85 g) gave 5-[2-[[[5-[(dimethylamino)methyl]-4-methyl-2-furanyl]methyl]thio]ethyl]-1-methyl-3-phenylmethyl-1H-1,2,4-triazole-5-amine (0.42 g) as a pale yellow oil.

T.l.c. System A $R_f$ 0.58.

N.m.r. (CDCl$_3$): 2.6–2.9,m, (5H); 4.06,s,(1H); 6.16,s,(2H); 5.53,t,(1H); 6.40,s,(2H), 6.58–6.61,m,(7H); 7.27,t,(2H); 7.8,s,(6H); 8.1,s,(3H);

(d) N-[2-(acetyloxy)acetyl]-1-methyl-2-phenylmethylene)hydrazinecarboximidothioate (B) (0.75 g) and 3-[3-[(1-hexamethyleneiminyl)methyl]phenoxy]-propanamine (0.64 g) gave 1-methyl-5-[3-[3-[(1-hexamethyleneiminyl)methyl]phenyl]propyl]amino-1H-1,2,4-triazole-3-methanol (0.32 g), m.p. 80°–82°.

N.m.r. (CDCl$_3$); 2.8,t,(1H); 3.0–3.3m, (3H); 5.42–5.45,m, (3H); 5.88–7.0,m,(11H); 7.4,m,(4H); 7.9,m,(2H); 8.4,m,(8H).

(e) B (1.37 g) and diamine C (1.0 g) gave 5-[[2-[[[5-[(dimethylamino)methyl]-2-thienyl]methyl]thio]ethyl]amino]-1-methyl-1H-1,2,4-triazole-3-methanol (0.2 g).

T.l.c. System B. R$_f$ 0.48.

N.m.r. (CDCl$_3$); 3.25,m,(2H); 5.1,m,(2H); 5.5,s,(2H); 6.16,s,(2H); 6.35–6.5,m, (7H); 7.22,t,(2H) 7.77,s,(6H).

(f) B (0.75 g) and 3-[3-(1-pyrrolidinylmethyl)phenoxy]propanamine (0.57 g) gave 1-methyl-5-[3-[3-(1-pyrrolidinylmethyl)phenoxy]propyl]amino]-1H-1,2,4-triazole-3-methanol (0.4 g) m.p. 105°–7° C.

Found: C, 62.9; H, 7.9; N, 20.7; C$_{18}$H$_{27}$N$_5$O$_2$ requires: C, 62.6; H, 7.9; M, 20.3%.

(g) B (0.75 g) and 5-[[(2-aminoethyl)thio]methyl]-3-N,N-trimethyl-2-furanmethanamine (0.5 g) gave 5-[[2-[[[5-[(dimethylamino)methyl]-4-methyl-2-furanyl]methyl]thio]ethyl]amino]-1-methyl-1H-1,2,4-triazole-3-methanol (0.32 g) T.l.c. System B R$_f$ 0.53. N.m.r. (CDCl$_3$) 4.02,s, (1H); 5.32–5.48,m,(3H); 6.37,s, (2H); 6.50–6.7,m,(7H); 7.25,t, (2H); 7.82,s,(6H); 8.08,s,(3H).

EXAMPLE 18

α,α,1-trimethyl-5-[[4-[3-(1-piperidinylmethyl)phenoxy]-butyl]amino]-1H-1,2,4-triazole-3-methanol N-[3-(1-hydroxy-1-methylethyl)-1-methyl-1H-1,2,4-triazole-5-yl]-4-[3-(1-piperidinylmethyl)phenoxy]-butanamide A solution of methyl 1-methyl-5-[[1-oxo-4-[3-(1-piperidinylmethyl)phenoxy]butyl]amino]-1H-1,2,4-triazole-3-carboxylate (508 mg) in tetrahydrofuran (10 ml) at −78° was treated with a solution of methyl magnesium iodine [(1.6 ml) of a solution prepared from magnesium turnings (400 mg) and methyl iodine (0.7 ml) in ether (10 ml)]. The mixture was maintained at −78° for 0.5 h. allowed to reach room temperature and quenched with water. The mixture was partitioned between ethyl acetate and 2N sodium hydroxide, the aqueous layer was extracted with ethyl acetate, and the combined organic extracts were dried and evaporated in vacuo. The residue was chromatographed to give the title compound (358 mg) as an oil.

T.l.c. System B. R$_f$0.8.

N.m.r. (CDCl$_3$): 2.82,t,(1H); 3.0–3.3,m,(4H); 6.0,t,(2H); 6.20,s,(1H); 6.32,s,(3H); 6.60,s, (2H); 7.3,m,(2H); 7.5–8.0,m,(6H); 8.45,s,(6H); 8.5,m,(6H).

α,α,1-trimethyl-5-[[4-[3-(1-piperidinylmethyl)phenoxy]-butyl]amino]-1H-1,2,4-triazole-3-methanol A stirred solution of N-[3-(1-hydroxy-1-methylethyl)-1-methyl-1H-1,2,4-triazol-5-yl]-4-[3-(1-piperidinylmethyl)phenoxy]butanamide (308 mg) in tetrahydrofuran (20 ml) under nitrogen was treated, with lithium aluminium hydride (0.5 g) in an ice-bath. The mixture was stirred at room temperature for 24 h, quenched with water and extracted with ethyl acetate. The combined organic extracts were dried and evaporated to give an oil (300 mg) which was chromatographed on silica using ethyl acetate:isopropanol:water:0.88 ammonia (25:15:8:2) to give the title compound (224 mg) as an oil. T.l.c. System B R$_f$ 0.7. N.m.r. (CDCl$_3$): 2.80,t,(1H); 3.0–3.3,m,(3H); 5.65,t,(1H); 6.02,s, (2H); 6.52,m,(7H); 7.60,m,(4H); 8.0–8.7,m,(10H); 8.46,s,(6H).

EXAMPLE 19

1-methyl-5-[[4-[3-(1-piperidinylmethyl)phenoxy]butyl]amino]-1H-1,2,4-triazole-3-methanamine A solution of methyl 1-methyl-5-[[1-oxo-4-[3-(1-piperidinylmethyl)phenoxy]butyl]amino]-1H-1,2,4-triazole-3-carboxylate (1.94 g) in 0.88 ammonia was stirred at room temperature for 18 h. The mixture was evaporated to yield a yellow foam, which was triturated with ether to give a yellow solid (1.56 g) which was used without further purification. A portion of this solid (1.20 g) was suspended in tetrahydrofuran (50 ml) and treated at room temperature with lithium aluminium hydride (1.0 g). The mixture was heated under reflux for 24 h, cooled and quenched with water. The resulting mixture was extracted with ethyl acetate, and the combined organic extracts were evaporated to yield an oil (0.90 g) which was chromatographed to give the title compound as an oil (210 mg).

T.l.c. System B R$_f$ 0.5. N.m.r. (D$_2$O); 2.5,t,(1H); 2.8–3.0,m,(3H); 5.43,s,(4H); 5.72,s,(2H); 5.8,t,(2H); 5.86,s,(2H); 6.47,s,(3H); 6.6,m,(4H); 7.05,bt,(2H); 8.0–8.6,m,(10H).

EXAMPLE 20

(a)

N,N-1-Trimethyl-5-[[4-[3-(1-piperidinylmethyl)phenoxy]butyl]amino]-1H-1,2,4-triazole-3-methanamine A solution of 1-methyl-5-[[4-[3-(1-piperidinylmethyl)phenoxy]butyl]amino]-1H-1,2,4-triazole-3-methanol (200 mg) in thionyl chloride (4 ml) was stirred at room temperature for 0.5 h. The mixture was evaporated to give a white foam which was used without further purification, and dissolved in a 33% solution of dimethylamine in ethanol (25 ml). The resulting solution was maintained at room temperature for 16 h, and evaporated to give an oil which was chromatographed on silica using ethyl acetate:isopropanol:water:0.88 ammonia (25:15:8:2) to give the title compound (132 mg) as an oil. T.l.c. System B. R$_f$0.6 N.m.r. (CDCl$_3$): 2.8,t,(1H); 3.0–3.3,m,(3H); 5.66,t,(1H); 6.02,t,(2H); 6.4–6.7,m, (9H); 7.6,m,(4H); 7.7,s.(6H); 8.0–8.7,m, (10H).

(b) Similarly prepared from the same triazole methanol (150 mg), thionyl chloride (3 ml) and 0.88 aqueous ammonia (50 ml) was 1-methyl-5-[[4-[3-(1-piperidinylmethyl)phenoxy]butyl]amino]-1H-1,2,4-triazole-3-methanamine (109 mg). T.l.c. System B and n.m.r. (D$_2$O) were the same as for the product of Example 19.

EXAMPLE 21

1-methyl-5-[[4-[3-(1-piperidinylmethyl)phenoxy]butyl]amino]-1H-1,2,4-triazole-3-methanol A stirred solution of 1-methyl-5-[[4-[3-(1-piperidinylmethyl)phenoxy]butyl]amino]-1H-1,2,4-triazole-3-methanol, acetate (5 mg) in ethanol (1 ml) was treated with 2N sodium hydroxide solution (0.5 ml). The mixture was maintained at room temperature for 2 h, evaporated in vacuo, and the residue was partitioned between ethyl acetate and water. The aquous layer was extracted with ethyl acetate and the combined organic extracts were dried and evaporated in vacuo to yield the title compound (4 mg) as a white solid, m.p. 82°-83°.
T.l.c. System B, R$_f$ identical to product of Example 7.

EXAMPLE 22

1-methyl-5-[[3-[3-[(1-piperidinyl)methyl]phenoxy]-propyl]amino]-1H-1,2,4-triazole-3-methanol 3-[3-(1-piperidinylmethyl)phenoxy]propanamine (1.24 g) and N-[2-acetyloxy)acetyl]-1-methyl-2-(phenylmethylene)hydrazinecarboximidothioate (1.535 g) were heated together at 50° for 3 h. The residual oil was used without purification, and dissolved in acetone (30 ml). 2N hydrochloric acid (5 ml) was added, the solution was stirred at room temperature for 1.5 h and left overnight without stirring. A further quantity of 2N hydrochloric acid (5 ml) was added and the solution was heated at reflux for 2 h. Water (50 ml) was added, the aqueous solution was washed with ethyl acetate, and basified with excess solid sodium carbonate. The basic solution was extracted with ethyl acetate, and the organic extracts were evaporated to give the title compound as a white solid (1.1 g) m.p. 119°.
T.l.c. System B, R$_f$ 0.7.

EXAMPLE 23

The following compound was prepared using the method of Example 10:
3-[4-(1-piperidinylmethyl)phenoxy]propanamine (0.61 g) and methyl N-[2-(acetyloxy)acetyl]-1-methyl-2-(phenylmethylene)hydrazinecarboximidothioate (0.75 g) gave 2-(acetyloxy)-N-[[[3-[4-(1-piperidinylmethyl)phenoxy]propyl]amino][1-methyl-(2-phenylmethylene)hydrazino]methylene]acetamide (1,2 g).
T.l.c. System A R$_f$ 0.59.
N.m.r. (CDCl$_3$) 2.2,s,(1H); 2.3–2.45,m, (2H); 2.5–2.75,m, (3H); 2.85,d,(2H); 3.2,d,(2H); 5.4,s,(2H); 5.9,t,(2H); 6.45,q,(2H); 6.6,s,(3H); 6.64,s,(2H); 7.55–7.8,m,(6H) 7.85,s,(3H); 8.3–8.6,m,(6H).

The above acetamide (1.2 g) was acidified to give 1-methyl-N-[[3-[4-(1-piperidinylmethyl)phenoxy]-propyl]amino]-1H-1,2,4-triazole-3-methanol.
T.l.c. System A. R$_f$ 0.6. N.m.r. (CDCl$_3$) 2.78,d,(2H) 3.20,d, (2H); 5.48,s, (2H); 5.94,t,(2H); 6.42,q,(2H); 6.52,s,(3H); 6.62,s,(2H); 6.8,br,s,(1H); 7.68,m,(4H) 7.9,m,(2H); 8.3–8.7,m, (6H).

EXAMPLE 24

α,1-dimethyl-N-[[4-[3-(1-piperidinylmethyl)phenoxy]-butyl]amino]-1H-1,2,4-triazole-3-methanol
1-Methyl-N-[[4-[3-(1-piperidinylmethyl)phenoxy]butyl]amino]-1H-1,2,4-triazole-3-carbaldehyde Dimethyl sulphoxide (304 mg) was added to a solution of oxalyl chloride (254 mg) in dichloromethane (20 ml) at −60° under nitrogen. The solution was stirred at −50° to −60° for 2 min and a solution of 1-methyl-N-[[4-[3-(1-piperidinylmethyl)phenoxy]butyl]amino]-1H-1,2,4 triazole-3-methanol (0.5 g) in dichloromethane (10 ml) was added. The mixture was stirred at −50° to −60° for 15 min and then quenched with triethylamine (657 mg). The solution was allowed to warm to 25° and was diluted with water. The aqueous phase was extracted with dichloromethane and the combined organic extracts were dried and evaporated to leave the title compound as a pale yellow oil (0.4 g). N.m.r. CDCl$_3$ 0.2,s,(1H); 2.78,t,(1H); 3.0–3.3,m,(3H); 5.25,br,t, (1H); 6.06, br t, (2H); 6.40,s,(3H); 6.5,q, (2H); 6.60,s, (2H); 7.68,br, (4H); 8.0–8.6,m, (10H). Tlc System A R$_f$ 0.55.

α,1-dimethyl-N-[[4-[3-(1-piperidinylmethyl)phenoxy]-butyl]amino]-1H-1,2,4-triazole-3-methanol A solution of methyl lithium [(0.6 m in ether), 10 ml] was added to a solution of the above carbaldehyde (0.4 g) in tetrahydrofuran (20 ml) at 25° under nitrogen. The mixture was stirred for 12 h, quenched with water and extracted with ethyl acetate. The combined organic extracts were evaporated to give a yellow oil (0.3 g).
Tlc System C R$_f$ 0.3.

EXAMPLE 25

Following the method of Example 17, N-[2-(acetyloxy)acetyl]-1-methyl-2-(phenylmethylene)hydrazinecarboximidothioate (0.75 g) and 3-[3-[1-(4-hydroxypiperidinyl)methyl]phenoxy]propanamine (0.65 g) gave 1-methyl-5-[[3-[3-[1-(4-hydroxypiperidinyl)methyl]phenoxy]propyl]amino]-1H-1,2,4-triazole-3-methanol (0.3 g), t.l.c. System B R$_f$ 0.4. N.m.r. (CDCl$_3$) 2.80,t,(1H); 3.0–3.3,m,(3H); 4.63,t,(1H); 5.52,s,(2H); 5.8–6.1,m,(5H); 6.3–6.7,m,(7H); 7.1–7.4,m,(2H) 7.7–8.7,m, (8H).

EXAMPLE 26

1-methyl-5-[3-[3-(1-piperidinylmethyl)phenoxy]-propyl]amino]-1H-1,2,4-triazole-3-one The following compound was prepared using the method of preparation 5: methyl 1-methyl-2-(phenylmethylene)hydrazinecarboximidothioatehydroiodide (2,35 g) and methylchloroformate (0.58 ml) gave methyl-N-methoxycarbonyl-1-methyl-2-(phenymethylene)hydrazinecarboximidothioate (0.65 g), m.p. 85°–6°.

The following compound was prepared using the method of Example 10:
3-[3-(1-piperidinylmethyl)phenoxy]propanamine (0.62 g) and methyl-N-methoxy carbonyl-1-methyl-2-(phenylmethylene)hydrazinecarboximidothioate (0.59 g) gave methyl[[1-methyl-2-(phenylmethylene)-hydrazino][[3-[3-(1-piperidinylmethyl)phenoxy]-propyl]amino]methylene]carbamate (0.9 g).
T.l.c. silica; methanol. R$_f$ 0.35.

The above carbamate (0.6 g) was acidified to give 1-methyl-[5-[3-[3-(1-piperidinylmethyl)phenoxy]-propyl]amino]-1H-1,2,4-triazole-3-one tartrate (0.03 g).
T.l.c. System B. R$_f$ 0.23.
N.m.r. (D$_2$O); 2.50,t,(1H); 2.8–3.0,m,(3H); 5.45,s,(2H); 5.8,s+m,(4H); 6.4–6.6,m,(4H); 6.73,s,(3H); 7.05,t,(2H); 7.7–8.6,m,(8H).

EXAMPLE 27

The following compound was prepared using the method of Example 17:
Methyl-N-[2-(acetyloxy)acetyl]-1-methyl-2-(phenylmethylene)hydrazinecarboximidothioate (0.75 g) and 3-(3 aminopropoxy)-N,N-dimethylbenzenemethanamine (0.51 g) gave 1-methyl-5-[[3-[3-[(dimethylamino)methyl]phenoxy]propyl]amino]-1H-1,2,4-trazole-3-methanol (0.3 g).
T.l.c. System B. R$_f$ 0.52.
N.m.r. (CDCl$_3$); 2.76,t,(1H); 3–3.3,m,(3H); 5.4–5.9,m, (6H); 6.42–6.64,m, (8H); 7.8–7.9,m,(8H).

EXAMPLE 28

5-[[3-[3-[(Phenylmethylamino)methyl]phenoxy]propyl]amino]-1H-1,2,4-triazole-3-methanol A solution of 5-[[3-(3-formylphenoxy)propyl]amino]-1-methyl-1H-1,2,4-triazole-3-methanol (532 mg) in ethanol (15 ml) was treated with benzylamine (5 ml) and stirred at room temperature for 1.5 h. The solution was treated with sodium borohydride (500 mg) and stirred at room temperature for 16 h. The mixture was evaporated, and the residue partitioned between 2N hydrochloric acid and ethyl acetate. The aqueous layer was washed with ethyl acetate, neutralised with potassium carbonate, and extracted with ethyl acetate. The combined extracts were dried and evaporated in vacuo to yield an oil. This oil was chromatographed on silica gel, using a mixture of methanol-ethyl acetate (1:1) to give the title compound as an oil (315 mg).

T.l.c. silica: methanol, $R_f$ 0.5.

N.m.r. (CDCl$_3$): 2.72,s+t,(6H); 3.0–3.3,m,(3H); 5.24,br.t,(1H); 5.52,s,(2H); 5.98,t,(2H); 6.1–6.7,m,(8H); 6.60,s,(3H); 7.98,m,(2H).

The following compound was similarly prepared from the above aldehyde (A) and 1-heptylamine.

(1) A (558 mg) and 1-heptylamine (5 ml) gave 5-[[3-[3-[(1-heptylamino)methyl]phenoxy]propyl]amino]-1H-1,2,4-triazole-3-methanol, as an oil (153 mg).

T.l.c. Silica; methanol $R_f$ 0.3.

N.m.r. (CDCl$_3$): 2.80,t,(1H); 3.1–3.3,m,(3H); 5.50,s+m,(3H); 5.97,t,(2H); 6.30,s,(2H); 6.50,q,(2H); 6.58,s,(3H); 6.90,bs,(2H); 7.41,t(2H); 7.96,m,(2H); 8.3–8.9,m,(10); 9.2,bt,(3H).

EXAMPLE 29

The following compounds were prepared using the method of Example 17.

(a) 4-[5-[(dimethylamino)methyl]-2-furanyl]butanamine (1.96 g) and methyl 1-methyl-N-phenyl-acetyl-2-(phenylmethylene)hydrazinecarboximidothioate (3.25 g) gave 5-[4-[5-[(dimethylamino)methyl]-2-furanyl]butyl]-1-methyl-3-phenylmethyl-1H-1,2,4-triazole-5-amine (2.0 g).

T.l.c. system B, $R_f$ 0.52.

N.m.r. (CDCl$_3$): 2.6–2.9,m,(5H); 3.98,d,(1H); 4.13,d,(1H); 5.80,t,(1H); 6.13,s,(2H); 6.13,s,(2H); 6.60–6.65,m,(7H); 7.38,t,(2H); 7.80,s,(6H); 8.3.m.(4H.

(b) 4-[5-[(Dimethylamino)methyl]-2-furanyl]butanamine (1.1 g) and N-[2-(acetyloxy)acetyl]-1-methyl-2-(phenylmethylene)hydrazinecarboximidothioate (1.9 g) gave 5-[[4-[-[(dimethylamino)methyl]-2-furanyl]butyl]amino]-1-methyl-1H-1,2,4-triazole-3-methanol (0.5 g) m.p. 88°–90°.

T.l.c. System C, $R_f$ 0.34.

Examples of Pharmaceutical compositions according to the invention are as follows:

| (a) TABLETS | mg/tablet | mg/tablet |
|---|---|---|
| Active ingredient | 20.0 | 40.0 |
| Microcrystalline cellulose BPC | 99.5 | 199.0 |
| Magnesium stearate B.P. | 0.5 | 1.0 |
| Compression weight | 120.0 | 240.0 |

The drug is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

| (b) CAPSULES | mg/capsule |
|---|---|
| Active ingredient | 20.0 |
| **Sta-Rx 1500 Starch | 79.5 |
| Magnesium Stearate B.P. | 0.5 |
| Fill weight | 100.0 |

**A form of directly compressible starch supplied by Colorcon Ltd, Orpington, Kent.

The active ingredient is sieved through a 250 μm sieve and blended with other materials. The mix is filled into No. 3. hard gelatin capsules using a suitable filling machine. Other doses may be prepared by increasing the fill weight and if necessary changing the capsule size to accommodate the increase.

| (c) SUSTAINED RELEASE TABLETS | mg/tablet |
|---|---|
| Active ingredient | 80 |
| *Cutina HR | 25 |
| Lactose B.P. | 142.5 |
| Magnesium Stearate B.P. | 2.5 |
| Compression weight | 250.0 |

*Cutina HR is a grade of microfine hydrogenated castor oil supplied by Sipon Products Ltd., London.

The drug is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 8.5 mm punches to produce tablets with a hardness of not less than 10 Kp (Schleuniger tester).

| (d) INJECTION FOR INTRAVENOUS ADMINISTRATION | % w/v |
|---|---|
| Active ingredient | 0.25 |
| Water for Injections BP to | 100.00 |

Sodium chloride may be added to adjust the tonicity of the solution and the pH may be adjusted to that of maximum stability using either dilute acid or alkali.

The solution is prepared, clarified and filled under nitrogen into appropriate sized ampoules sealed by fusion of the glass. The injection is sterilised by heating in an autoclave using one of the acceptable cycles. Alternatively the solution may be sterilised by filtration and filled into sterile ampoules under aseptic conditions.

| (e) SYRUP | mg/5 ml dose |
|---|---|
| Active ingredient | 20.0 mg |
| Sucrose | 2750.0 mg |
| Glycerine | 500.0 mg |
| Buffer | |
| Flavour | |
| Colour | as necessary |
| Preservative | |
| Distilled water to | 5.0 ml |

The active ingredient, buffer, flavour, preservative and colour are dissolved in some of the water. The remainder of the water is heated to approximately 80° C. and the sucrose is dissolved in this and cooled. The two solutions are mixed, adjusted to volume and clarified by filtration.

EXAMPLE 30

(a)
1-Methyl-5-[[3-[3-(1-piperidinylmethyl)phenoxy]-propyl]amino]-1H-1,2,4-triazole-3-methanol, sulphate (1:1)

1-Methyl-5-[[3-[3-(1-piperidinylmethyl)phenoxy]-propyl]amino]-1H-1,2,4-triazole-3-methanol (300 mg) was dissolved in ethyl acetate (20 ml) with heating and the addition of a few drops of ethanol to give a clear solution. A 0.45 ml aliquot of a hot solution of concentrated sulphuric acid (1 ml) in ethanol (9 ml) was added dropwise. The solid which separated on cooling and standing was filtered off, washed with diethyl ester and dried in vacuo to give the title compound as a white crystalline solid (400 mg), m.p. 170°.

In a similar manner:
(b) A solution of the free base (300 mg) as in (a) above was treated with a hot solution of tartaric acid (125 mg) in ethanol (10 ml) to give the tartrate salt (2:1) as a white crystalline solid (50 mg), m.p. 144°.

(c) A solution of the free base (300 mg) as in (a) above was treated with a hot solution of succinic acid (99 mg) in ethanol (10 ml) to give the succinate salt (2:1) as a white crystalline solid (150 mg), m.p. 137°.

We claim:
1. Compounds of the general formula (I)

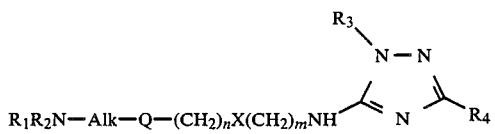

and physiologically acceptable salts, hydrates; and tautomers thereof, in which $R_1$ and $R_2$, which may be the same or different, each represent hydrogen, $C_{1-10}$ alkyl, $C_{3-8}$ cycloalkyl, $C_{3-6}$ alkenyl, aralkyl in which the alkyl moiety contains 1 to 6 carbon atoms; trifluoro $C_{1-6}$ alkyl, or $C_{1-6}$ alkyl substituted by hydroxy, $C_{1-6}$ alkoxy, amino, $C_{1-6}$ alkylamino or di $C_{1-6}$ alkylamino or $R_1$ and $R_2$ may together with the nitrogen atom to which they are attached form a heterocyclic ring which is pyrrolidine, piperidine optionally substituted in the 4-position by $C_{1-3}$ alkyl or hydroxy; tetrahydropyridine, morpholine, 2,6-di $C_{1-6}$ alkylmorpholine, hexamethyleneimine or heptamethylenimine;

Alk represents a straight or branched alkylene chain of 1 to 6 carbon atoms;

Q represents a furan or thiophene ring in which incorporation into the rest of the molecule is through bonds at the 2- and 5-positions, the furan ring optionally bearing a further substituent $R_6$ adjacent to the group $R_1R_2N$—Alk—, or Q represents a benzene ring in which incorporation into the rest of the molecule is through bonds at the 1- and 3- or 1- and 4-positions;

$R^6$ represents halogen or $C_{1-4}$ alkyl which may be substituted by hydroxy or $C_{1-4}$ alkoxy;

X represents —$CH_2$—, —O—, —S— or

where $R_5$ represents hydrogen or methyl;

n represents zero, 1 or 2;

m represents 2, 3 or 4;

$R_3$ represents hydrogen, $C_{1-6}$ alkyl, $C_{3-6}$ alkenyl, ar $C_{1-6}$ alkyl, hydroxy $C_{2-6}$ alkyl, $C_{1-6}$ alkoxy $C_{1-6}$ alkyl or phenyl optionally substituted by one or more $C_{1-3}$ alkyl or alkoxy groups or halogen atoms; and $R_4$ represents hydrogen, $C_{1-6}$ alkyl, $C_{3-6}$ alkenyl, phenyl optionally substituted by one or more $C_{1-3}$ alkyl or alkoxy groups or halogen atoms; aralkyl in which the alkyl moiety contains 1 to 6 carbon atoms; hydroxy $C_{1-6}$ alkyl, acyloxy $C_{1-6}$ alkyl in which the acyl portion is $C_{1-6}$ alkanoyl, benzoyl optionally substituted by 1 or more $C_{1-3}$ alkyl or alkoxy groups or halogen atoms, or aralkanoyl in which the alkyl moiety contains 1 to 6 carbon atoms; $C_{1-6}$ alkoxy $C_{1-6}$ alkyl, aryloxy $C_{1-6}$ alkyl, ar $C_{1-6}$ alkyloxy $C_{1-6}$ alkyl; amino $C_{1-6}$ alkyl, $C_{1-6}$ alkyl-amino $C_{1-6}$ alkyl, di $C_{1-6}$ alkylamino $C_{1-6}$ alkyl, hydroxy, $C_{1-6}$ alkoxy, $C_{1-6}$ alkythio or halogen and wherein aryl or as a group or part of a group is phenyl optionally substituted by one or more $C_{1-3}$ alkyl or alkoxy groups or halogen atoms.

2. Compounds of the general formula (I)

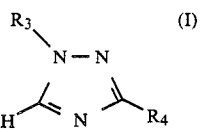

and physiologically acceptable salts, hydrates; and tautomers thereof, in which $R_1$ and $R_2$, which may be the same or different, each represent hydrogen, $C_{1-10}$ alkyl, $C_{3-8}$ cycloalkyl, $C_{3-6}$ alkenyl, ar $C_{1-6}$ alkyl; trifluoro $C_{1-6}$ alkyl, or $C_{1-6}$ alkyl substituted by hydroxy, $C_{1-6}$ alkoxy, amino, $C_{1-6}$ alkylamino or di $C_{1-6}$ alkylamino or $R_1$ and $R_2$ may together with the nitrogen atom to which they are attached form a heterocyclic ring which is pyrrolidine, piperidine optionally substituted in the 4-position by $C_{1-3}$ alkyl or hydroxy; tetrahydropyridine, morpholine, 2,6-dialkylmorpholine, hexamethyleneimine or heptamethylenimine;

Alk represents a straight or branched alkylene chain of 1 to 6 carbon atoms;

Q represents a furan or thiophene ring in which incorporation into the rest of the molecule is through bonds at the 2- and 5-positions, the furan ring optionally bearing a further substituent $R_6$ adjacent to the group $R_1R_2N$—Alk—, or Q represents a benzene ring in which incorporation into the rest of the molecule is through bonds at the 1- and 3- or 1- and 4-positions;

$R^6$ represents halogen or $C_{1-4}$ alkyl which may be substituted by hydroxy or $C_{1-4}$ alkoxy;

X represents —$CH_2$—, —O—, —S— or

where $R_5$ represents hydrogen or methyl;

n represents zero, 1 or 2;

m represents 2, 3 or 4;

$R_3$ represents hydrogen, $C_{1-6}$ alkyl, $C_{3-6}$ alkenyl, ar $C_{1-6}$ alkyl; hydroxy $C_{2-6}$ alkyl, $C_{1-6}$ alkoxy $C_{1-6}$ alkyl or phenyl optionally substituted by one or more $C_{1-3}$ alkyl or alkoxy groups or halogen atoms; and $R_4$ represents hydrogen, $C_{1-6}$ alkyl, $C_{3-6}$ alkenyl, phenyl optionally substituted by one or more $C_{1-3}$ alkyl or alkoxy groups or halogen atoms; ar $C_{1-6}$ alkyl, hydroxy $C_{1-6}$ alkyl, $C_{1-6}$ alkoxy $C_{1-6}$ alkyl, aryloxy $C_{1-6}$ alkyl, amino $C_{1-6}$ alkyl, $C_{1-6}$ alkyl-amino $C_{1-6}$ alkyl, di $C_{1-6}$ alkylamino $C_{1-6}$ alkyl, hydroxy, $C_{1-6}$ alkoxy, or halogen; provided that when X represents an oxygen atom or —$NR_5$— and when n is zero then Q represents benzene; and wherein aryl or ar as a group or part of a group is phenyl optionally substituted by one or more $C_{1-3}$ alkyl or alkoxy groups or halogen atoms.

3. Compounds according to claims 1 or 2 in which Q represents benzene incorporated into the molecule through bonds at the 1- and 3-positions, n is zero and X is oxygen.

4. Compounds according to claims 1 or 2 in which m+n is 3 or 4.

5. Compounds according to claims 1 or 2 in which Alk is —$CH_2$—.

6. Compounds according to claims 1 or 2 in which $R_1$ represents hydrogen or $C_{1-4}$ alkyl and $R_2$ represents $C_{3-5}$ alkenyl, $C_{5-7}$ cycloalkyl, benzyl, $C_{1-8}$ alkyl or $C_{1-4}$ alkyl substituted by $C_{1-3}$ alkoxy, hydroxy, di-$C_{1-3}$ alkylamino or trifluoromethyl or $R_1$ and $R_2$ together with the nitrogen atom to which they are attached form a heterocyclic ring which is pyrrolidine, piperidine optionally substituted in the 4-position by $C_{1-3}$ alkyl or hydroxy; tetrahydropyridine, morpholine, 2,6-dialkylmorpholine, hexamethyleneimine or heptamethylenimine.

7. Compounds according to claim 6 in which $R_1$ and $R_2$ represent $C_{1-3}$ alkyl, or $R_1$ and $R_2$ together with the nitrogen atom to which they are attached form a heterocyclic ring which is pyrrolidine, piperidine optionally substituted in the 4-position by methyl or hydroxy, tetrahydropyridine, morpholine, 2,6-dimethylmorpholine, hexamethyleneimine or heptamethylenimine.

8. Compounds according to claims 1 or 2 in which $R_3$ represents hydrogen, $C_{1-6}$ alkyl or hydroxy $C_{2-4}$ alkyl.

9. Compounds according to claim 1 in which $R_4$ represents hydrogen, $C_{1-6}$ alkyl, hydroxy $C_{1-6}$ alkyl, $C_{1-6}$ alkoxy $C_{1-6}$ alkyl, acyloxy $C_{1-6}$ alkyl in which the acyl portion is $C_{1-6}$ alkanoyl, benzoyl, optionally substituted by one or more $C_{1-3}$ alkyl or alkoxy groups or halogen atoms; or aralkanoyl in which the alkyl moiety contains 1 to 6 carbon atoms and the aryl group is phenyl optionally substituted by one or more $C_{1-3}$ alkyl or alkoxy groups or halogen atoms, aralkyl in which the alkyl moiety contains 1 to 6 carbon atoms and the aryl group is phenyl optionally substituted by one or more $C_{1-3}$ alkyl or alkoxy groups or halogen atoms, or hydroxy.

10. Compounds according to claim 2 in which $R_4$ represents hydrogen, $C_{1-6}$ alkyl, hydroxy $C_{1-6}$ alkyl, $C_{1-6}$ alkoxy $C_{1-6}$ alkyl, ar $C_{1-6}$ alkyl in which the aryl group is phenyl optionally substituted by one or more $C_{1-3}$ alkyl or alkoxy groups or halogen atoms; or hydroxy.

11. Compounds according to claim 9 or claim 10 in which $R_4$ represents hydroxy $C_{1-6}$ alkyl, hydroxy, $C_{1-6}$ alkoxy $C_{1-6}$ alkyl, or benzyl.

12. Compounds according to claims 1 or 2, corresponding to the formula (II)

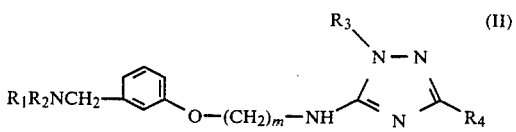

where $R_1$ and $R_2$ are methyl groups or together with the nitrogen atom to which they are attached form a pyrrolidino, piperidino or hexamethyleneimino group; m is 3 or 4; $R_3$ is hydrogen or methyl, and $R_4$ is a hydroxy $C_{1-6}$ alkyl, $C_{1-6}$ alkoxy $C_{1-6}$ alkyl, benzyl, or hydroxy.

13. Compounds which are:
1-methyl-5-[[4-[3-(1-piperidinylmethyl)phenoxy]butyl]amino]-1H-1,2,4-triazole-3-methanol,
1-methyl-5-[[3-[3-(1-piperidinylmethyl)phenoxy]propyl]amino]-1H-1,2,4-triazole-3-methanol,
3-methoxy-methyl-1-methyl-5-[[4-[3-(1-piperidinylmethyl)phenoxy]butyl]amino]-1H-1,2,4-triazole or their physiologically acceptable salts.

14. Compounds which are:
3-phenylmethyl-N-[3-[3-(dimethylaminomethyl)phenoxy]propyl]-1H-1,2,4-triazole-5-amine
5-[4-[3-(1-piperidinylmethyl)phenoxy]butyl]amino-1H-1,2,4-triazole-3-methanol,
3-phenylmethyl-N-[3-[3-(1-piperidinylmethyl)phenoxy]propyl]-1H-1,2,4-triazole-5-amine,
5-[[3-[3-(1-piperidinylmethyl)phenoxy]propyl]amino]-1H-1,2,4-triazole-3-one, or their physiologically acceptable salts.

15. 5-[[2-[[[5-[(dimethylamino)methyl]-2-furanyl]methyl]thio]ethyl]amino]-1-methyl-1H-1,2,4-triazole-3-methanol and physiologically acceptable salts thereof.

16. 5-[2-[[[5-[(dimethylamino)methyl]-4-methyl-2-furanyl]methyl]thio]ethylamino]amino]-1-methyl-1H-1,2,4-triazole-3-methanol and physiologically acceptable salts thereof.

17. 1-methyl-5-[[3-[3-[(dimethylamino)methyl]phenoxy]propyl]amino]-1H-1,2,4-triazole-3-methanol and physiologically acceptable salts thereof.

18. Compounds according to any of claims 1, 2, 15, 16 or 17 in the form of a hydrochloride, hydrobromide, sulphate, methanesulphonate, acetate, maleate, succinate, citrate, fumarate, benzoate or tartrate salt.

19. Compounds according to claim 1 corresponding to the formula

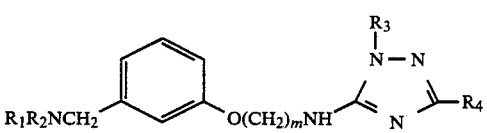

where $R_1$ represents hydrogen or $C_{1-4}$ alkyl and $R_2$ represents $C_{3-5}$ alkenyl, $C_{5-7}$ cycloalkyl, benzyl, $C_{1-8}$ alkyl; $C_{1-4}$ alkyl substituted by $C_{1-3}$ alkoxy, hydroxy, di-$C_{1-3}$ alkylamino or trifluoromethyl, or $R_1$ and $R_2$ together with the nitrogen atom to which they are attached form a heterocyclic ring which is pyrrolidine, piperidine optionally substituted in the 4-position by $C_{1-3}$ alkyl or hydroxy, tetrahydropyridine, morpholine, 2,6-di $C_{1-6}$ alkylmorpholine, hexamethyleneimine or heptamethyleneimine; m is 3 or 4; $R_3$ represents hydrogen, $C_{1-6}$ alkyl or $C_{2-4}$ hydroxyalkyl; and $R_4$ represents hydrogen, $C_{1-6}$ alkyl, hydroxy $C_{1-6}$ alkyl, $C_{1-6}$ alkoxy $C_{1-6}$ alkyl, acyloxy $C_{1-6}$ alkyl in which the acyl portion is $C_{1-6}$ alkanoyl, benzoyl optionally substituted by one or more $C_{1-3}$ alkyl or alkoxy groups or halogen atoms, or aralkanoyl in which the alkyl moiety contains 1 to 6 carbon atoms and the aryl group is phenyl optionally substituted by one or more $C_{1-3}$ alkyl or alkoxy groups or halogen atoms; aralkyl in which the alkyl portion contains 1 to 6 carbon atoms and the aryl group is phenyl optionally substituted by one or more $C_{1-3}$ alkyl or alkoxy groups or halogen atoms; or hydroxy.

20. Compounds according to claim 2 in which $R_4$ represents hydrogen, $C_{1-6}$ alkyl, hydroxy $C_{1-6}$ alkyl, $C_{1-6}$ alkoxy $C_{1-6}$ alkyl, aralkyl in which the alkyl moiety contains 1 to 6 carbon atoms and the aryl group is phenyl optionally substituted by one or more $C_{1-3}$ alkyl or alkoxy groups or halogen atoms; or hydroxy.

21. Compounds according to claim 20 corresponding to the formula

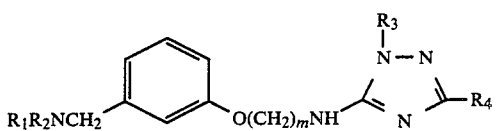

where $R_1$ represents hydrogen or $C_{1-4}$ alkyl and $R_2$ represents $C_{3-5}$ alkenyl, $C_{5-7}$ cycloalkyl, benzyl, $C_{1-8}$ alkyl; $C_{1-4}$ alkyl substituted by $C_{1-3}$ alkoxy, hydroxy, di-$C_{1-3}$ alkylamino or trifluoromethyl, or $R_1$ and $R_2$ together with the nitrogen atom to which they are attached form a heterocyclic ring which is pyrrolidine, piperidine optionally substituted in the 4-position by $C_{1-3}$ alkyl or hydroxy, tetrahydropyridine, morpholine, 2,6-di $C_{1-6}$ alkylmorpholine, hexamethyleneimine or heptamethyleneimine; m is 3 or 4; $R_3$ represents hydrogen, $C_{1-6}$ alkyl or $C_{2-4}$ hydroxyalkyl; and $R_4$ represents hydrogen, $C_{1-6}$ alkyl, hydroxy $C_{1-6}$ alkyl, $C_{1-6}$ alkoxy $C_{1-6}$ alkyl or hydroxy.

22. A pharmaceutical composition comprising an effective amount of a compound for the treatment of conditions mediated through $H_2$ receptors wherein said compound is as claimed in any of claims 1, 2, 15, 16 or 17 together with at least one pharmaceutically acceptable carrier or diluent, and optionally one or more further active ingredients.

23. A pharmaceutical composition according to claim 15 in a form adapted for oral administration.

24. A pharmaceutical composition according to claim 22 containing 5 mg to 1 g of the compound of formula (I).

25. A method of treating a condition mediated through histamine $H_2$-receptors which comprises administering to a patient an effective amount of a composition as defined in claim 15 to relieve said condition.

* * * * *